(12) United States Patent
Zhuang et al.

(10) Patent No.: US 8,564,792 B2
(45) Date of Patent: Oct. 22, 2013

(54) SUB-DIFFRACTION LIMIT IMAGE RESOLUTION IN THREE DIMENSIONS

(75) Inventors: Xiaowei Zhuang, Cambridge, MA (US);
Bo Huang, San Francisco, CA (US);
Wilfred M. Bates, Goettingen (DE);
Wenqin Wang, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/746,784

(22) PCT Filed: Dec. 19, 2008

(86) PCT No.: PCT/US2008/013915
§ 371 (c)(1),
(2), (4) Date: Aug. 30, 2010

(87) PCT Pub. No.: WO2009/085218
PCT Pub. Date: Jul. 9, 2009

(65) Prior Publication Data
US 2011/0002530 A1   Jan. 6, 2011

Related U.S. Application Data

(60) Provisional application No. 61/008,661, filed on Dec. 21, 2007.

(51) Int. Cl.
*G01B 11/14* (2006.01)
(52) U.S. Cl.
USPC .......................................... 356/624; 356/614
(58) Field of Classification Search
USPC .......... 356/614, 624, 456, 496, 311, 317–318, 356/402, 417, 36; 436/164, 172, 171, 514; 250/458.1–461.2
See application file for complete search history.

(56) References Cited

U.S. PATENT DOCUMENTS

| 6,008,373 A | 12/1999 | Waggoner et al. |
| 6,537,829 B1 | 3/2003 | Zarling et al. |

(Continued)

FOREIGN PATENT DOCUMENTS

| JP | 2002-062261 A | 2/2002 |
| JP | 2007-140322 A | 6/2007 |

(Continued)

OTHER PUBLICATIONS

Office Action mailed Jun. 12, 2009 for U.S. Appl. No. 12/012,524.

(Continued)

*Primary Examiner* — Tri T Ton
(74) *Attorney, Agent, or Firm* — Wolf, Greenfield & Sacks, P.C.

(57) ABSTRACT

The present invention generally relates to sub-diffraction limit image resolution and other imaging techniques, including imaging in three dimensions. In one aspect, the invention is directed to determining and/or imaging light from two or more entities separated by a distance less than the diffraction limit of the incident light. In some cases, the position of the entities can be determined in all three spatial dimensions (i.e., in the x, y, and z directions), and in certain cases, the positions in all three dimensions can be determined to an accuracy of less than about 1000 nm. In some cases, the z positions may be determined using one of a variety of techniques that uses intensity information or focal information (e.g., a lack of focus) to determine the z position. Non-limiting examples of such techniques include astigmatism imaging, off-focus imaging, or multi-focal-plane imaging.

27 Claims, 14 Drawing Sheets

(56) References Cited

U.S. PATENT DOCUMENTS

| | | |
|---|---|---|
| 7,430,045 B2 | 9/2008 | Hell et al. |
| 7,535,012 B2 | 5/2009 | Betzig et al. |
| 7,626,694 B2 | 12/2009 | Hess et al. |
| 7,626,695 B2 | 12/2009 | Hess et al. |
| 7,626,703 B2 | 12/2009 | Hess et al. |
| 7,710,563 B2 | 5/2010 | Betzig et al. |
| 7,776,613 B2 | 8/2010 | Zhuang et al. |
| 7,782,457 B2 | 8/2010 | Hess et al. |
| 7,828,695 B2 | 11/2010 | Inoue et al. |
| 7,838,302 B2 | 11/2010 | Zhuang et al. |
| 7,864,314 B2 | 1/2011 | Betzig et al. |
| 2002/0064789 A1 | 5/2002 | Weiss et al. |
| 2003/0087282 A1 | 5/2003 | Oshida et al. |
| 2006/0038993 A1 | 2/2006 | Hell |
| 2008/0032414 A1 | 2/2008 | Zhuang et al. |
| 2008/0068588 A1 | 3/2008 | Hess et al. |
| 2008/0068589 A1 | 3/2008 | Hess et al. |
| 2008/0070322 A1 | 3/2008 | Hess et al. |
| 2008/0070323 A1* | 3/2008 | Hess et al. ............ 436/514 |
| 2008/0111086 A1 | 5/2008 | Betzig et al. |
| 2008/0182336 A1 | 7/2008 | Zhuang et al. |
| 2009/0206251 A1 | 8/2009 | Hess et al. |
| 2010/0181497 A1 | 7/2010 | Hess et al. |
| 2010/0231922 A1 | 9/2010 | Hess et al. |
| 2010/0283835 A1 | 11/2010 | Bewersdorf et al. |
| 2010/0297777 A1 | 11/2010 | Zhuang et al. |
| 2010/0316269 A1 | 12/2010 | Zhuang et al. |
| 2012/0009589 A1 | 1/2012 | Zhuang et al. |
| 2013/0001436 A1 | 1/2013 | Zhuang et al. |

FOREIGN PATENT DOCUMENTS

| | | |
|---|---|---|
| WO | WO 01/96373 A2 | 12/2001 |
| WO | WO 2004/090617 A2 | 10/2004 |
| WO | WO 2006/127692 A2 | 11/2006 |
| WO | WO 2008/091296 A2 | 7/2008 |
| WO | WO 2009/085218 A1 | 7/2009 |

OTHER PUBLICATIONS

Office Action mailed Jan. 15, 2010 for U.S. Appl. No. 12/012,524.
Notice of Allowance mailed Jul. 19, 2010 for U.S. Appl. No. 12/012,524.
Office Action mailed Apr. 29, 2009 for U.S. Appl. No. 11/605,842.
Office Action mailed Nov. 6, 2009 for U.S. Appl. No. 11/605,842.
Notice of Allowance mailed May 20, 2010 for U.S. Appl. No. 11/605,842.
European Office Communication dated Jun. 15, 2009 for Application EP 07872605.6.
International Preliminary Report on Patentability mailed Feb. 19, 2009 for International Patent Application No. PCT/US07/017618.
International Search Report and Written Opinion mailed Dec. 15, 2008 for International Patent Application No. PCT/US07/017618.
International Search Report mailed Apr. 23, 2009 for International Patent Application No. PCT/US2008/013915.
Written Opinion mailed Apr. 23, 2009 for International Patent Application No. PCT/US2008/013915.
International Preliminary Report on Patentability mailed Jun. 22, 2010 for International Patent Application No. PCT/US2008/013915.
Amato, Squint-Busters: Tool builders are pushing optical microscope vision to single-molecule sharpness. Chemical and Engineering News. Sep. 4, 2006;49-52.
Ando et al., Regulated fast nucleocytoplasmic shuttling observed by reversible protein highlighting. Science. Nov. 19, 2004;306(5700):1370-3.
Antonik et al., Separating structural heterogeneities from stochastic variations in fluorescence resonance energy transfer distributions via photon distribution analysis. J Phys Chem B. Apr. 6, 2006;110(13):6970-8.
Bates et al., Short-range spectroscopic ruler based on a single-molecule optical switch. Phys Rev Lett. Mar. 18, 2005;94(10):108101. Epub Mar. 15, 2005.
Bates et al., Super-resolution microscopy by nanoscale localization of photo-switchable fluorescent probes. Curr Opin Chem Biol. Oct. 2008;12(5):505-14.
Bates et al., Multicolor super-resolution imaging with photo-switchable fluorescent probes. Science. Sep. 21, 2007;317(5845):1749-53. Epub Aug. 16, 2007.
Betzig, Proposed method for molecular optical imaging. Opt Lett. Feb. 1, 1995;20(3):237-9.
Betzig et al., Imaging intracellular fluorescent proteins at nanometer resolution. Science. Sep. 15, 2006;313(5793):1642-5. Epub Aug. 10, 2006.
Betzig et al., Imaging intracellular fluorescent proteins at nanometer resolution. (Supporting Online Material), http://www.sciencemag.org/cgi/content/full/1127344/DC1, pp. 1-30 (2006).
Dailey et al., Confocal Microscopy of Living Cells. 2006;Handbook of Biological Confocal Microscopy. $3^{rd}$ ed. Chapter 19, pp. 381-403.
Friedman et al., Viewing dynamic assembly of molecular complexes by multi-wavelength single-molecule fluorescence. Biophys J. Aug. 1, 2006;91(3):1023-31. Epub May 12, 2006.
Habuchi et al., Reversible single-molecule photoswitching in the GFP-like fluorescent protein Dronpa. Proc Natl Acad Sci U S A. Jul. 5, 2005;102(27):9511-6. Epub Jun. 22, 2005.
Hell et al., Breaking the diffraction resolution limit by stimulated emission: stimulated-emission-depletion fluorescence microscopy. Opt Lett. Jun. 1, 1994;19(11):780-2.
Hess et al., Ultra-high resolution imaging by fluorescence photoactivation localization microscopy. Biophys J. Dec. 1, 2006;91(11):4258-72. Epub Sep. 15, 2006.
Hofmann et al., Breaking the diffraction barrier in fluorescence microscopy at low light intensities by using reversibly photoswitchable proteins. Proc Natl Acad Sci U S A. Dec. 6, 2005;102(49):17565-9. Epub Nov. 28, 2005.
Huang et al., Three-dimensional super-resolution imaging by stochastic optical reconstruction microscopy. Science. Feb. 8, 2008;319(5864):810-3. Epub Jan. 3, 2008.
Huang et al., Whole-cell 3D STORM reveals interactions between cellular structures with nanometer-scale resolution. Nat Methods. Dec. 2008;5(12):1047-52. Epub Nov. 23, 2008.
Juette et al., Three-dimensional sub-100 nm resolution fluorescence microscopy of thick samples. Nat Methods. Jun. 2008;5(6):527-9. Epub May 11, 2008.
Kao et al., Tracking of single fluorescent particles in three dimensions: use of cylindrical optics to encode particle position. Biophys J. Sep. 1994;67(3):1291-300.
Lacoste et al., Ultrahigh-resolution multicolor colocalization of single fluorescent probes. Proc Natl Acad Sci U S A. Aug. 15, 2000;97(17):9461-6.
Pavani et al., Three-dimensional, single-molecule fluorescence imaging beyond the diffraction limit by using a double-helix point spread function. Proc Natl Acad Sci U S A. Mar. 3, 2009;106(9):2995-9. Epub Feb. 11, 2009.
Prabhat et al., Simultaneous imaging of several focal planes in fluorescence microscopy for the study of cellular dynamics in 3D. Proc of SPIE. 2006;6090:60900L-1-60900L-7.
Rust et al., Sub-diffraction-limit imaging by stochastic optical reconstruction microscopy (STORM). Nat Methods. Oct. 2006;3(10):793-5. Epub Aug. 9, 2006.
Schmidt et al., Mitochondrial cristae revealed with focused light. Nano Lett. Jun. 2009;9(6):2508-10.
Schmidt et al., Spherical nanosized focal spot unravels the interior of cells. Nat Methods. Jun. 2008;5(6):539-44. Epub May 18, 2008.
Shtengel et al., Interferometric fluorescence super-resolution microscopy resolves 3D cellular ultrastructure. Proc Natl Acad Sci U S A. Mar. 3, 2009;106(9):3125-30. Epub Feb. 6, 2009.
Speidel et al., Three-dimensional tracking of fluorescent nanoparticles with subnanometer precision by use of off-focus imaging. Opt Lett. Jan. 15, 2003;28(2):69-71.
Toprak et al., Three-dimensional particle tracking via bifocal imaging. Nano Lett. Jul. 2007;7(7):2043-5. Epub Jun. 21, 2007.
Van Oijen et al., 3-Dimensional super-resolution by spectrally selective imaging. Chemical Physics Letters. 1998;292:183-187.

(56) References Cited

OTHER PUBLICATIONS

Vaziri et al., Multilayer three-dimensional super resolution imaging of thick biological samples. Proc Natl Acad Sci U S A. Dec. 23, 2008;105(51):20221-6. Epub Dec. 16, 2008.
Wang et al., Label-free detection of small-molecule-protein interactions by using nanowire nanosensors. Proc Natl Acad Sci U S A. Mar. 1, 2005;102(9):3208-12. Epub Feb. 16, 2005.
Jones et al., Fast, three-dimensional super-resolution imaging of live cells. Nat Methods. Jun. 2011;8(6):499-505. Epub May 8, 2011.
Zhuang, Nano-imaging with STORM. Nat Photonics. 2009;3(7):365-367.
Notice of Allowance mailed Sep. 13, 2010 for U.S. Appl. No. 12/012,524.
Eisenstein, New fluorescent protein includes handy on-off switch. Nature Methods. 2005;2(1):8-9.
Hell et al., Imaging and writing at the nanoscale with focused visible light through saturable optical transitions. Applied Physics. 2003;77(7):859-60.
Hell et al., Concepts for nanoscale resolution in fluorescence microscopy. Curr Opin Neurobiol. Oct. 2004;14(5):599-609.
Frontiers in live cell imaging/NIGMS and the Cell Migration Consortium (Movie). National Institute of General Medical Sciences, Apr. 20, 2006, http://videocast.nih.gov/launch.asp?13187.
European Office Communication mailed Sep. 30, 2010 for Application EP 07872605.6.
European Office Communication mailed Mar. 14, 2012 for Application EP 07872605.6.
Partial European Seach Report for EP 11169771.0 mailed Mar. 14, 2012.
Extended European Seach Report for 11169771.0 mailed Jul. 6, 2012.
Japanese Office Communication mailed Apr. 11, 2012 for JP Application No. 2009-523831.
Chinese Office Action mailed Sep. 27, 2011 for Chinese Application No. 200880121492.2.
Chinese Office Action mailed Jun. 6, 2012 for Chinese Application No. 200880121492.2.
Advisory Action mailed Jun. 28, 2010 for U.S. Appl. No. 12/012,524.
Office Action mailed Apr. 17, 2012 for U.S. Appl. No. 12/795,423.
Office Action mailed Jul. 16, 2012 for U.S. Appl. No. 12/850,586.
Office Action mailed Feb. 29, 2012 for U.S. Appl. No. 13/179,936.
Aquino et al., Two-color nanoscopy of three-dimensional volumes by 4Pi detection of stochastically switched fluorophores. Nat Methods. Apr. 2011;8(4):353-9. Epub Mar. 13, 2011.
Gruber et al., Anomalous fluorescence enhancement of Cy3 and cy3.5 versus anomalous fluorescence loss of Cy5 and Cy7 upon covalent linking to IgG and noncovalent binding to avidin. Bioconjug Chem. Sep.-Oct. 2000;11(5):696-704.
Gugel et al., Cooperative 4Pi excitation and detection yields sevenfold sharper optical sections in live-cell microscopy. Biophys J. Dec. 2004;87(6):4146-52. Epub Sep. 17, 2004.
Gustafsson et al., I5m: 3D widefield light microscopy with better than 100 nm axial resolution. J Microsc. Jul. 1999;195(Pt 1):10-6.
Gustafsson et al., Sevenfold improvement of axial resolution in 3D widefield microscopy using two objective lenses. Proceedings of SPIE. 1995;2412:147-56. Month not listed on copy of publication.
Heilemann et al., Carbocyanine dyes as efficient reversible single-molecule optical switch. J Am Chem Soc. Mar. 23, 2005;127(11):3801-6.
Hell et al., Properties of a 4Pi confocal fluorescence microscope. J Opt Soc Am A. Dec. 1992;9(12):2159-66.
Ram et al., Improved single particle localization accuracy with dual objective multifocal plane microscopy. Opt Express. Apr. 13, 2009;17(8):6881-98.
Widengren et al., Characterization of Photoinduced Isomerization and Back-Isomerization of the Cyanine Dye Cy5 by Fluorescence Correlation Spectroscopy. J Phys Chem A. 2000;104 (27):6416-6428. Month not listed on copy of publication.
Xu et al., Dual-objective STORM reveals three-dimensional filament organization in the actin cytoskeleton. Nat Methods. Jan. 8, 2012;9(2):185-8. doi: 10.1038/nmeth.1841.
Xu et al., Dual-objective STORM reveals three-dimensional filament organization in the actin cytoskeleton. Nat Methods. Jan. 8, 2012;9(2):185-8. doi: 10.1038/nmeth.1841. Supplementary Information.
Chinese Office Action mailed Nov. 19, 2012 for Chinese Application No. 200880121492.2.
Office Action mailed Oct. 9, 2012 for U.S. Appl. No. 12/795,423.
Office Action mailed Oct. 18, 2012 for U.S. Appl. No. 13/179,936.
Held, An Introduction to Fluorescence Resonance Energy Transfer (FRET) Technology and its Application in Bioscience. BioTek®. Jun. 15, 2005. Available at http://www.biotek.com/resources/docs/Fluorescence_Resonance_Energy_Transfer_Technology_FRET_App_Note.pdf. 8 pages.
Office Action mailed Oct. 18, 2012 for JP Application No. 2010-539499.
Japanese Office Action mailed Feb. 27, 2013 for JP Application No. 2009-523831.
Japanese Office Action mailed Mar. 1, 2013 for JP Application No. 2012-178598.
Invitation to Pay Additional Fees for Application No. PCT/US2012/069138 mailed Apr. 2, 2013.
Final Office Action mailed Apr. 4, 2013 for U.S. Appl. No. 12/795,423.
Office Action mailed Jan. 30, 2013 for U.S. Appl. No. 12/850,586.
Final Office Action mailed Apr. 11, 2013 for U.S. Appl. No. 13/179,936.
Office Action mailed Feb. 11, 2013 for U.S. Appl. No. 13/551,357.
Cyan-to-green photoswitchable fluorescent protein PS-CFP2. 2008. <http://www.evrogen.com/protein-descriptions/PS-CFP2-description.pdf>.
Aitken et al., an oxygen scavenging system for improvement of dye stability in single-molecule fluorescence experiments. Biophys J. Mar. 1, 2008;94(5):1826-35. Epub Oct. 5, 2007.
Andresen et al., Photoswitchable fluorescent proteins enable monochromatic multilabel imaging and dual color fluorescence nanoscopy. Nat Biotechnol. Sep. 2008;26(9):1035-40.
Centonze et al., Fluorescence resonance energy transfer imaging microscopy. Methods Enzymol. 2003;360:542-60. Month not cited on publication.
Dos Remedios et al., Fluorescence resonance energy transfer spectroscopy is a reliable "ruler" for measuring structural changes in proteins. Dispelling the problem of the unknown orientation factor. J Struct Biol. Sep.-Oct. 1995;115(2):175-85.
Fluorescence Resonance Energy Transfer (FRET) Microscopy. Olympus Microscopy Resource Center, 2012.
Kenworthy et al., Imaging protein-protein interactions using fluorescence resonance energy transfer microscopy. Methods. Jul. 2001;24(3):289-96.
Linde et al., Photoswitching microscopy with subdiffraction-resolution. Proc SPIE. Feb. 24, 2009;7185:71850F1-11.
Osterman et al., White Paper: Near-infrared fluorescence imaging: Seeing beyond the visible with IRDye infrared dyes. 2012. Available at http://biosupport.licor.com/docs/IRDyes—HOPaper_v8.pdf. Last accessed Feb. 25, 2013. 18 pages. Month not cited on publication.
Souslova et al., Photoswitchable cyan fluorescent protein as a FRET donor. Microsc Res Tech. Mar. 2006;69(3):207-9.
Truong et al., The use of FRET imaging microscopy to detect protein-protein interactions and protein conformational changes in vivo. Curr Opin Struct Biol. Oct. 2001;11(5):573-8.
Van De Linde et al., Multicolor photoswitching microscopy for subdiffraction-resolution fluorescence imaging. Photochem Photobiol Sci. Apr. 2009 ;8(4):465-9. Epub Feb. 9, 2009.
Yildiz et al., Fluorescence imaging with one nanometer accuracy: Application to molecular motors. Acc Chem Res. 2005;38(7):574-82. Published online Mar. 23, 2005.

* cited by examiner

SUB-DIFFRACTION LIMIT IMAGE RESOLUTION IN THREE DIMENSIONS

RELATED APPLICATIONS

This application is a U.S. National Stage Application of PCT/US2008/013915, filed Dec. 19, 2008, entitled "Sub-Diffraction Limit Image Resolution in Three Dimensions," by Zhuang, et al., which claims the benefit of U.S. Provisional Patent Application Ser. No. 61/008,661, filed Dec. 21, 2007, entitled "Sub-Diffraction Limit Image Resolution in Three Dimensions," by Zhuang, et al., each incorporated herein by reference.

GOVERNMENT FUNDING

This invention was made with U.S. Government support under GM068518 awarded by the National Institutes of Health. The U.S. Government has certain rights in the invention.

FIELD OF INVENTION

The present invention generally relates to sub-diffraction limit image resolution and other imaging techniques, including imaging in three dimensions.

BACKGROUND

Fluorescence microscopy is widely used in molecular and cell biology and other applications for non-invasive, time-resolved imaging. Despite these advantages, standard fluorescence microscopy is not useful for ultra-structural imaging, due to a resolution limit set by the diffraction of light. Several approaches have been employed to try to pass this diffraction limit, including near-field scanning optical microscopy (NSOM), stimulated emission depletion (STED), reversible saturable optical linear fluorescence transition (RESOLFT), and saturated structured-illumination microscopy (SSIM), but each has certain unsatisfactory limitations. Electron microscopy is often used for high resolution imaging of biological samples, but electron microscopy uses electrons, rather than light, and is difficult to use with biological samples due to its preparation requirements. Accordingly, new techniques, including non-invasive techniques are needed to harness the benefits of fluorescence microscopy, for ultra-resolution imaging of biological and other samples, e.g., to allow molecular specificity and/or compatibility with live biological samples.

SUMMARY OF THE INVENTION

The present invention generally relates to sub-diffraction limit image resolution and other imaging techniques, including imaging in three dimensions. The subject matter of the present invention involves, in some cases, interrelated products, alternative solutions to a particular problem, and/or a plurality of different uses of one or more systems and/or articles.

In one aspect, the invention is directed to a method. In one set of embodiments, the method includes acts of providing a first entity and a second entity separated by a distance of less than about 1000 nm, determining light emitted by the first entity, determining light emitted by the second entity, and determining x, y, and z positions of the first entity and the second entity using the light emitted by the first entity and the light emitted by the second entity. The method, in another set of embodiments, includes acts of providing a first entity and a second entity separated by a distance of separation, determining light emitted by the first entity, determining light emitted by the second entity, and determining x, y, and z positions of the first entity and the second entity using the light emitted by the first entity and the light emitted by the second entity.

According to yet another set of embodiments, the method includes acts of providing a first entity and a second entity separated by a distance of less than about 1000 nm, activating the first entity but not the second entity, determining light emitted by the first entity, activating the second entity, determining light emitted by the second entity, and determining x, y, and z positions of the first entity and the second entity using the light emitted by the first entity and the light emitted by the second entity. In still another set of embodiments, the method includes acts of providing a first entity and a second entity separated by a distance of separation, activating the first entity but not the second entity, determining light emitted by the first entity, activating the second entity, determining light emitted by the second entity, and determining x, y, and z positions of the first entity and the second entity using the light emitted by the first entity and the light emitted by the second entity.

In one set of embodiments, the method includes acts of providing a plurality of entities able to emit light (at least some of which are separated by a distance of less than about 1000 nm), activating a fraction of the plurality of entities to emit light, determining the emitted light, deactivating the activated fraction of the plurality of entities, and repeating the acts of activating and deactivating the plurality of entities to determine x, y, and z positions of the plurality of entities. The method, in yet another set of embodiments, includes acts of providing a plurality of entities able to emit light, activating a fraction of the plurality of entities to emit light, determining the emitted light, deactivating the activated fraction of the plurality of entities, and repeating the acts of activating and deactivating the plurality of entities to determine x, y, and z positions of the plurality of entities.

In another aspect, the present invention is directed to a method of making one or more of the embodiments described herein. In another aspect, the present invention is directed to a method of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figures 1A, 1B:
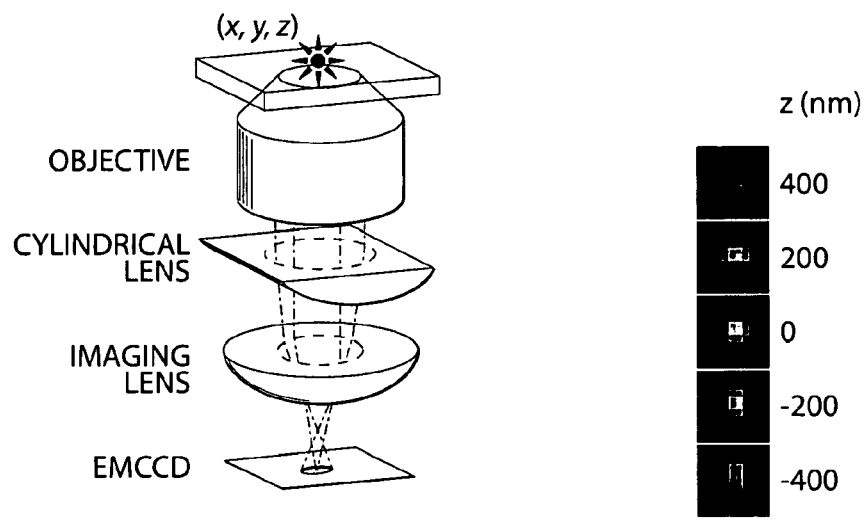
FIGS. 1A-1G illustrate one embodiment of the invention, useful for determining the position of an entity in three dimensions.

The present invention generally relates to sub-diffraction limit image resolution and other imaging techniques, including imaging in three dimensions. In one aspect, the invention is directed to determining and/or imaging light from two or more entities separated by a distance less than the diffraction limit of the incident light. For example, the entities may be separated by a distance of less than about 1000 nm, or less than about 300 nm for visible light. In some cases, the position of the entities can be determined in all three spatial dimensions (i.e., in the x, y, and z directions), and in certain cases, the positions in all three dimensions can be determined to an accuracy of less than about 1000 nm. In one set of embodiments, the entities may be selectively activatable, i.e., one entity can be activated to produce light, without activating other entities. A first entity may be activated and determined (e.g., by determining light emitted by the entity), then a second entity may be activated and determined. The emitted light may be used to determine the x and y positions of the first and second entities, for example, by determining the positions of the images of these entities, and in some cases, with sub-diffraction limit resolution. In some cases, the z positions may be determined using one of a variety of techniques that uses intensity information or focal information (e.g., a lack of focus) to determine the z position. Non-limiting examples of such techniques include astigmatism imaging, off-focus imaging, or multi-focal-plane imaging. Other aspects of the invention relate to systems for sub-diffraction limit image resolution, computer programs and techniques for sub-diffraction limit image resolution, methods for promoting sub-diffraction limit image resolution, and the like.

One aspect of the invention is generally directed to techniques for resolving two or more entities, even at distances of separation that are less than the wavelength of the light emitted by the entities or below the diffraction limit of the emitted light. The resolution of the entities may be, for instance, on the order of 1 micrometer (1000 nm) or less, as described herein. For example, if the emitted light is visible light, the resolution may be less than about 700 nm. In some cases, two (or more) entities may be resolved even if separated by a distance of less than about 500 nm, less than about 300 nm, less than about 200 nm, less than about 100 nm, less than about 80 nm, less than about 60 nm, less than about 50 nm, or less than about 40 nm. In some cases, two or more entities separated by a distance of less than about 20 nm or less than 10 nm can be resolved using embodiments of the present invention.

The entities may be any entity able to emit light. For instance, the entity may be a single molecule. Non-limiting examples of emissive entities include fluorescent entities (fluorophores) or phosphorescent entities, for example, cyanine dyes (e.g., Cy2, Cy3, Cy5, Cy5.5, Cy7, etc.) metal nanoparticles, semiconductor nanoparticles or "quantum dots," or fluorescent proteins such as GFP (Green Fluorescent Protein). Other light-emissive entities are readily known to those of ordinary skill in the art. As used herein, the term "light" generally refers to electromagnetic radiation, having any suitable wavelength (or equivalently, frequency). For instance, in some embodiments, the light may include wavelengths in the optical or visual range (for example, having a wavelength of between about 400 nm and about 1000 nm, i.e., "visible light"), infrared wavelengths (for example, having a wavelength of between about 300 micrometers and 700 nm), ultraviolet wavelengths (for example, having a wavelength of between about 400 nm and about 10 nm), or the like. In certain cases, as discussed in detail below, more than one entity may be used, i.e., entities that are chemically different or distinct, for example, structurally. However, in other cases, the entities may be chemically identical or at least substantially chemically identical.

In some cases, one or more of the entities is "switchable," i.e., the entity can be switched between two or more states, at least one of which emits light having a desired wavelength. In the other state(s), the entity may emit no light, or emit light at a different wavelength. For instance, an entity may be "activated" to a first state able to produce light having a desired wavelength, and "deactivated" to a second state. In some cases, at least one of these entities are photoactivatable or photoswitchable. An entity is "photoactivatable" if it can be activated by incident light of a suitable wavelength. An entity is "photoswitchable" if it can be switched between different light-emitting or non-emitting states by incident light of different wavelengths. Typically, a "switchable" entity can be identified by one of ordinary skill in the art by determining conditions under which an entity in a first state can emit light when exposed to an excitation wavelength, switching the entity from the first state to the second state, e.g., upon exposure to light of a switching wavelength, then showing that the entity, while in the second state can no longer emit light (or emits light at a reduced intensity) or emits light at a different wavelength when exposed to the excitation wavelength. Examples of switchable entities are discussed in detail below, and are also discussed in International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008, incorporated herein by reference.

In some aspects, the light may be processed to determine the spatial positions of the two or more entities. In some cases, the positions of one or more entities, distributed within an image, may each be individually determined, and in some cases, the positions of the entities may be determined in 3 dimensions (i.e., in the x, y, and z dimensions, where the z dimension is the direction of the optical axis of the imaging system and the x and y dimensions are perpendicular to the z direction, and to each other). In one set of embodiments, the emitted light may be processed, using Gaussian fitting or other suitable techniques, to localize the position of each of the emissive entities. Details of one suitable Gaussian fit technique are described in the Examples, below; those of ordinary skill in the art will be able to identify other suitable image-processing techniques with the benefit of the present disclosure.

Another example of an image-processing technique follows, in accordance with another embodiment of the invention. Starting with a series of images of a sample (e.g., a movie), each light-emission peak (e.g., through fluorescence, phosphorescence, etc.) is identified, and the times which the peak is present are determined. For example, a peak may be present with approximately the same intensity in a series of images with respect to time. Peaks may be fit, in some cases, to Gaussian and/or elliptical Gaussian functions to determine their centroid positions, intensities, widths, and/or ellipticities. Based on these parameters, peaks which are too dim, too wide, too skewed, etc. to yield satisfactory localization accuracy may be rejected in certain cases from further analysis. Peaks which are sporadic, moving, discontinuously present, etc. may also be discarded. By determining the center position of the peak, for example, using least-squares fitting to a 2-dimensional Gaussian function of the peak intensities, the location of the source of the peak (e.g., any entity or entities able to emit light, as discussed herein) can be determined. This process may be repeated as necessary for any or all of the peaks within the sample.

In one set of embodiments, the z position of an entity can be determined at a resolution that is less than the diffraction limit of the incident light. For example, for visible light, the z position of an entity can be determined at a resolution less than about 800 nm, less than about 500 nm, less than about 200 nm, less than about 100 nm, less than about 50 nm, less than about 20 nm, or less than about 10 nm. Any microscopy technique able to determine the z position of entity may be used, for instance, astigmatism imaging, off-focus imaging, multi-focal plane imaging, confocal microscopy, two-photon microscopy, or the like. In some cases, the entity may be positioned and imaged such that the entity does not appear as a single point of light, but as an image that has some area, for example, as a slightly unresolved or unfocused image. As an example, the entity may be imaged by a lens or a detector system that defines one or more focal regions (e.g., one or more focal planes) that do not contain the entity, such that the image of the entity at the detector appears unfocused. The degree to which the entity appears unfocused can be used to determine the distance between the entity and one of the focal regions, which can then be used to determine the z position of the entity.

In one embodiment, the z position can be determined using astigmatism imaging. A lens may be used that is not circularly symmetric with respect to the direction light emitted by the entity passes through the lens. For instance, the lens may be cylindrical (as is shown in FIG. 1A), ellipsoidal, or the like. In some cases, the lens may have different radii of curvature in different planes. The light emitted by the entity after passing through the imaging optical system which includes this non-circularly symmetric lens may appear circular or elliptical at the detector.

The size and ellipticity of the image can be used, in some cases, to determine the distance between the entity and the focal region of the lens or the detector, which can then be used to determine the z position. As a non-limiting example, as shown in FIG. 1B, an image in focus (z=0 nm) appears circular, while images that are out of focus appear increasingly elliptical (z=±200 nm or ±400 nm), with the direction of ellipticity indicating whether the entity is above or below the focal region.

In another embodiment, the z position can be determined using off-focus imaging. An entity not in one of the focal regions defined by a lens or a detector system used to image the entity may appear to be unfocused, and the degree that the image appears unfocused may be used to determine the distance between the entity and the focal region of the lens, which can then be used to determine the z position. In some cases, the image of the unfocused entity may appear generally circular (with the area being indicative of the distance between the entity and the focal region of the lens), and in some instances, the image of the unfocused entity may appear as a series of ring-like structures, with more rings indicating greater distance).

In some embodiments, e.g., with multi-focal plane imaging, the light emitted by the entities may be collected by a plurality of detectors. In some cases, at one or more of the detectors, the light may appear to be unfocused. The degree that the images appear unfocused may be used to determine the z position.

In another non-limiting example of a suitable imaging processing technique of the present invention, a series of images of a sample (e.g. a movie) may include a repetitive sequence of activation frames (e.g., in which the activation light is on) and imaging frames (e.g., in which the imaging light is on). For one or more of the imaging frames, fluorescent peaks on each frame can be determined to determine their positions, intensities, widths, ellipticities, etc. Based on these parameters, peaks that are too dim, too wide, too skewed, etc. to yield satisfactory localization accuracy may be rejected from further analysis. Peaks which are sporadic, moving, discontinuously present, etc. may also be discarded in some cases. By determining the center position, the shape, and/or the size of the peak, the location of the source of the peak (e.g., any entity or entities able to emit light, as discussed herein) can be determined. In some cases, the position may be determined in 3 dimensions. This process may also be repeated as necessary for any or all of the peaks within the sample.

Other image-processing techniques may also be used to facilitate determination of the entities, for example, drift correction or noise filters may be used. Generally, in drift correction, for example, a fixed point is identified (for instance, as a fiduciary marker, e.g., a fluorescent particle may be immobilized to a substrate), and movements of the fixed point (i.e., due to mechanical drift) are used to correct the determined positions of the switchable entities. In another example method for drift correction, the correlation function between images acquired in different imaging frames or activation frames can be calculated and used for drift correction. In some embodiments, the drift may be less than about 1000 nm/min, less than about 500 nm/min, less than about 300 nm/min, less than about 100 nm/min, less than about 50 nm/min, less than about 30 nm/min, less than about 20 nm/min, less than about 10 nm/min, or less than 5 nm/min. Such drift may be achieved, for example, in a microscope having a translation stage mounted for x-y positioning of the sample slide with respect to the microscope objective. The slide may be immobilized with respect to the translation stage using a suitable restraining mechanism, for example, spring loaded clips. In addition, a buffer layer may be mounted between the stage and the microscope slide. The buffer layer may further restrain drift of the slide with respect to the translation stage, for example, by preventing slippage of the slide in some fashion. The buffer layer, in one embodiment, is a rubber or polymeric film, for instance, a silicone rubber film. Accordingly, one embodiment of the invention is directed to a device, comprising a translation stage, a restraining mechanism (e.g., a spring loaded clip) attached to the translation stage able to immobilize a slide, and optionally, a buffer layer (e.g., a silicone rubber film) positioned such that a slide restrained by the restraining mechanism contacts the buffer layer. To stabilize the microscope focus during data acquisition, a "focus lock" device may be used in some cases. As a non-limiting example, to achieve focus lock, a laser beam may be reflected from the substrate holding the sample and the reflected light may be directed onto a position-sensitive detector, for example, a quadrant photodiode. In some cases, the position of the reflected laser, which may be sensitive to the distance between the substrate and the objective, may be fed back to a z-positioning stage, for example a piezoelectric stage, to correct for focus drift.

In one set of embodiments, as discussed, a switchable entity may be used. Non-limiting examples of switchable entities are discussed in International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008, incorporated herein by reference. As a non-limiting example of a switchable entity, Cy5 can be switched between a fluorescent and a dark state in a controlled and reversible manner by light of different wavelengths, e.g., 633 nm or 657 nm red light can switch or deactivate Cy5 to a stable dark state, while 532 nm green light can switch or activate the Cy5 back to the fluorescent state. Other non-limiting examples of a switchable entity including photoactivatable or photoswitchable fluorescent proteins, or photoactivatable or photoswitchable inorganic particles, e.g., as discussed herein. In some cases, the entity can be reversibly switched between the two or more states, e.g., upon exposure to the proper stimuli. For example, a first stimuli (e.g., a first wavelength of light) may be used to activate the switchable entity, while a second stimuli (e.g., a second wavelength of light) may be used to deactivate the switchable entity, for instance, to a non-emitting state. Any suitable method may be used to activate the entity. For example, in one embodiment, incident light of a suitable wavelength may be used to activate the entity to emit light, i.e., the entity is photoswitchable. Thus, the photoswitchable entity can be switched between different light-emitting or non-emitting states by incident light, e.g., of different wavelengths. The light may be monochromatic (e.g., produced using a laser) or polychromatic. In another embodiment, the entity may be activated upon stimulation by electric field and/or magnetic field. In other embodiments, the entity may be activated upon exposure to a suitable chemical environment, e.g., by adjusting the pH, or inducing a reversible chemical reaction involving the entity, etc. Similarly, any suitable method may be used to deactivate the entity, and the methods of activating and deactivating the entity need not be the same. For instance, the entity may be deactivated upon exposure to incident light of a suitable wavelength, or the entity may be deactivated by waiting a sufficient time.

In some embodiments, the switchable entity includes a first, light-emitting portion (e.g., a fluorophore), and a second portion that activates or "switches" the first portion. For example, upon exposure to light, the second portion of the switchable entity may activate the first portion, causing the first portion to emit light. Examples of activator portions include, but are not limited to, Alexa Fluor 405 (Invitrogen), Alexa 488 (Invitrogen), Cy2 (GE Healthcare), Cy3 (GE Healthcare), Cy3.5 (GE Healthcare), or Cy5 (GE Healthcare), or other suitable dyes. Examples of light-emitting portions include, but are not limited to, Cy5, Cy5.5 (GE Healthcare), or Cy7 (GE Healthcare), Alexa Fluor 647 (Invitrogen), or other suitable dyes. These may linked together, e.g., covalently, for example, directly, or through a linker, e.g., forming compounds such as, but not limited to, Cy5-Alexa Fluor 405, Cy5-Alexa Fluor 488, Cy5-Cy2, Cy5-Cy3, Cy5-Cy3.5, Cy5.5-Alexa Fluor 405, Cy5.5-Alexa Fluor 488, Cy5.5-Cy2, Cy5.5-Cy3, Cy5.5-Cy3.5, Cy7-Alexa Fluor 405, Cy7-Alexa Fluor 488, Cy7-Cy2, Cy7-Cy3, Cy7-Cy3.5, or Cy7-Cy5. The structures of Cy3, Cy5, Cy5.5, and Cy 7 are shown in FIG. 6 with a non-limiting example of a linked version of Cy3-Cy5 shown in FIG. 6E; those of ordinary skill in the art will be aware of the structures of these and other compounds, many of which are available commercially.

Any suitable method may be used to link the first, light-emitting portion and the second, activation portion. In some cases, a linker is chosen such that the distance between the first and second portions is sufficiently close to allow the activator portion to activate the light-emitting portion as desired, e.g., whenever the light-emitting portion has been deactivated in some fashion. Typically, the portions will be separated by distances on the order of 500 nm or less, for example, less than about 300 nm, less than about 100 nm, less than about 50 nm, less than about 20 nm, less than about 10 nm, less than about 5 nm, less than about 2 nm, less than about 1 nm, etc. Examples of linkers include, but are not limited to, carbon chains (e.g., alkanes or alkenes), polymer units, or the like.

In certain cases, the light-emitting portion and the activator portions, when isolated from each other, may each be fluorophores, i.e., entities that can emit light of a certain, emission wavelength when exposed to a stimulus, for example, an excitation wavelength. However, when a switchable entity is formed that comprises the first fluorophore and the second fluorophore, the first fluorophore forms a first, light-emitting portion and the second fluorophore forms an activator portion that switches that activates or "switches" the first portion in response to a stimulus. For example, the switchable entity may comprise a first fluorophore directly bonded to the second fluorophore, or the first and second entity may be connected via a linker or a common entity. Whether a pair of light-emitting portion and activator portion produces a suitable switchable entity can be tested by methods known to those of ordinary skills in the art. For example, light of various wavelength can be used to stimulate the pair and emission light from the light-emitting portion can be measured to determined wither the pair makes a suitable switch.

Accordingly, in one embodiment of the invention, a light-emitting switchable entity is provided, comprising a first, light emitting portion and a second, activation portion. The entity has a maximum emission wavelength determined by the first, light emitting portion and a maximum activation wavelength determined by the second, activation portion. Notably, the two wavelengths are not controlled by the same molecular entity, and are effectively decoupled. In some cases, the same wavelength light can be used both for activating the emitting portion to a fluorescent state and for exciting emission from and deactivating the emitting portion. Further, multiple types of switchable entities within a sample may be independently determined. For example, two switchable entities having the same activator portions but different light-emission portions can be activated by the same wavelength light applied to the sample, but emit at different wavelengths due to different light-emission portions and can be easily distinguished, even at separation distances of less than sub-diffraction limit resolutions. This can effectively yield two colors in the image. Similarly, two switchable entities having the same light-emission portions but different activator portions can be activated by different wavelength light applied to the sample, due to the different activator portions, and the light-emission portions may emit at same wavelengths and can thus be distinguished, even at separation distances of less than sub-diffraction limit resolutions. This also can effectively yield two colors in the image. When these methods are combined, four (or more) color images can be readily produced. Using this principle, multi-color imaging can be scaled up to 6 colors, 9 colors, etc., depending on the switchable and/or activator entities. This multi-color imaging principle may also be used with the imaging methods described herein to yield sub-diffraction limit resolutions (in all three dimensions in some cases), and/or used to obtained multi-color images with other imaging methods not limited to sub-diffraction limit resolutions.

In some embodiments, the first, light-emitting portion and the second, activation portion as described above may not be directly covalently bonded or linked via a linker, but are each immobilized relative to a common entity. In other embodiments, two or more of the switchable entities (some of which can include, in certain cases, a first, light-emitting portion and a second, activation portion linked together directly or through a linker) may be immobilized relative to a common entity in some aspects of the invention. The common entity in any of these embodiments may be any nonbiological entity or biological entity, for example, a cell, a tissue, a substrate, a surface, a polymer, a biological molecule such as a nucleic acid (DNA, RNA, PNA, LNA, or the like), a lipid molecule, a protein or a polypeptide, or the like, a biomolecular complex, or a biological structure, for example, an organelle, a microtubule, a clathrin-coated pit, etc.

In one set of embodiments, the switchable entity can be immobilized, e.g., covalently, with respect to a binding partner, i.e., a molecule that can undergo binding with a particular analyte. Binding partners include specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair, the ligand would specifically and/or preferentially select its receptor from a complex mixture of molecules, or vice versa. Other examples include, but are not limited to, an enzyme would specifically bind to its substrate, a nucleic acid would specifically bind to its complement, an antibody would specifically bind to its antigen. The binding may be by one or more of a variety of mechanisms including, but not limited to ionic interactions, and/or covalent interactions, and/or hydrophobic interactions, and/or van der Waals interactions, etc. By immobilizing a switchable entity with respect to the binding partner of a target molecule or structure (e.g., DNA or a protein within a cell), the switchable entity can be used for various determination or imaging purposes. For example, a switchable entity having an amine-reactive group may be reacted with a binding partner comprising amines, for example, antibodies, proteins or enzymes.

In some embodiments, more than one switchable entity may be used, and the entities may be the same or different. In some cases, the light emitted by a first entity and the light emitted by a second entity have the same wavelength. The entities may be activated at different times and the light from each entity may be determined separately. This allows the location of the two entities to be determined separately and, in some cases, the two entities may be spatially resolved, as discussed in detail below, even at distances of separation that are less than the wavelength of the light emitted by the entities or below the diffraction limit of the emitted light (i.e., "sub-diffraction limit" resolutions). In certain instances, the light emitted by a first entity and the light emitted by a second entity have different wavelengths (for example, if the first entity and the second entity are chemically different, and/or are located in different environments). The entities may be spatially resolved even at distances of separation that are less than the wavelength of the light emitted by the entities or below the diffraction limit of the emitted light. In certain instances, the light emitted by a first entity and the light emitted by a second entity have substantially the same wavelengths, but the two entities may be activated by light of different wavelengths and the light from each entity may be determined separately. The entities may be spatially resolved even at distances of separation that are less than the wavelength of the light emitted by the entities, or below the diffraction limit of the emitted light.

In some cases, the entities may be independently switchable, i.e., the first entity may be activated to emit light without activating a second entity. For example, if the entities are different, the methods of activating each of the first and second entities may be different (e.g., the entities may each be activated using incident light of different wavelengths). As another non-limiting example, if the entities are substantially the same, a sufficiently weak intensity may be applied to the entities such that only a subset or fraction of the entities within the incident light are activated, i.e., on a stochastic or random basis. Specific intensities for activation can be determined by those of ordinary skill in the art using no more than routine skill. By appropriately choosing the intensity of the incident light, the first entity may be activated without activating the second entity. As another non-limiting example, the sample to be imaged may comprise a plurality of entities, some of which are substantially identical and some of which are substantially different. In this case, one or more of the above methods may be applied to independently switch the entities.

Light emitted by each of the entities may be determined, e.g., as an image or matrix. For example, the first entity may be activated and the light emitted by the first entity determined, and the second entity may be activated (with or without deactivating the first entity) and light emitted by the second entity may be determined. The light emitted by each of the plurality of entities may be at the same or different wavelengths. Any suitable method may be used to determine the emitted light. For instance, a detector of the light may be, for instance, a camera such as a CCD camera, a photodiode, a photodiode array, a photomultiplier, a photomultiplier array, a spectrometer, or the like; those of ordinary skill in the art will know of other suitable techniques. In some cases, more than one detector may be used, and the detectors may each independently be the same or different. In some cases, multiple images (or other determinations) may be used, for example, to improve resolution and/or to reduce noise. For example, at least 2, at least 5, at least 10, at least 20, at least 25, at least 50, at least 75, at least 100, etc. images may be determined, depending on the application.

In some cases, incident light having a sufficiently weak intensity may be applied to a plurality of entities such that only a subset or fraction of the entities within the incident light are activated, e.g., on a stochastic or random basis. The amount of activation may be any suitable fraction, e.g., about 0.1%, about 0.3%, about 0.5%, about 1%, about 3%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95% of the entities may be activated, depending on the application. For example, by appropriately choosing the intensity of the incident light, a sparse subset of the entities may be activated such that at least some of them are optically resolvable from each other and their positions can be determined. In some embodiments, the activation of the subset of the entities can be synchronized by applying a short duration of the incident light. Iterative activation cycles may allow the positions of all of the entities, or a substantial fraction of the entities, to be determined. In some cases, an image with sub-diffraction limit resolution can be constructed using this information.

Multiple locations on a sample may each be analyzed to determine the entities within those locations. For example, a sample may contain a plurality of various entities, some of which are at distances of separation that are less than the wavelength of the light emitted by the entities or below the diffraction limit of the emitted light. Different locations within the sample may be determined (e.g., as different pixels within an image), and each of those locations independently analyzed to determine the entity or entities present within those locations. In some cases, the entities within each location may be determined to resolutions that are less than the wavelength of the light emitted by the entities or below the diffraction limit of the emitted light, as previously discussed.

In some embodiments of the invention, the entities may also be resolved as a function of time. For example, two or more entities may be observed at various time points to determine a time-varying process, for example, a chemical reaction, cell behavior, binding of a protein or enzyme, etc. Thus, in one embodiment, the positions of two or more entities may be determined at a first point of time (e.g., as described herein), and at any number of subsequent points of time. As a specific example, if two or more entities are immobilized relative to a common entity, the common entity may then be determined as a function of time, for example, time-varying processes such as movement of the common entity, structural and/or configurational changes of the common entity, reactions involving the common entity, or the like. The time-resolved imaging may be facilitated in some cases since a switchable entity can be switched for multiple cycles, each cycle give one data point of the position of the entity.

Another aspect of the invention is directed to a computer-implemented method. For instance, a computer and/or an automated system may be provided that is able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. The processing steps may also be recorded onto a machine-readable medium in some cases.

Still another aspect of the invention is generally directed to a system able to perform one or more of the embodiments described herein. For example, the system may include a microscope, a device for activating and/or switching the entities to produce light having a desired wavelength (e.g., a laser or other light source), a device for determining the light emitted by the entities (e.g., a camera, which may include color-filtering devices, such as optical filters), and a computer for determining the spatial positions of the two or more entities. In some cases, mirrors (such as dichroic mirror or a polychroic mirror), prisms, lens, diffraction gratings, or the like may be positioned to direct light from the light source. In some cases, the light sources may be time-modulated (e.g., by shutters, acoustic optical modulators, or the like). Thus, the light source may be one that is activatable and deactivatable in a programmed or a periodic fashion. In one embodiment, more than one light source may be used, e.g., which may be used to illuminate a sample with different wavelengths or colors. For instance, the light sources may emanate light at different frequencies, and/or color-filtering devices, such as optical filters or the like may be used to modify light coming from the light sources such that different wavelengths or colors illuminate a sample.

In some embodiments, a microscope may be configured so to collect light emitted by the switchable entities while minimizing light from other sources of fluorescence (e.g., "background noise"). In certain cases, imaging geometry such as, but not limited to, a total-internal-reflection geometry a spinning-disc confocal geometry, a scanning confocal geometry, an epi-fluorescence geometry, etc., may be used for sample excitation. In some embodiments, a thin layer or plane of the sample is exposed to excitation light, which may reduce excitation of fluorescence outside of the sample plane. A high numerical aperture lens may be used to gather the light emitted by the sample. The light may be processed, for example, using filters to remove excitation light, resulting in the collection of emission light from the sample. In some cases, the magnification factor at which the image is collected can be optimized, for example, when the edge length of each pixel of the image corresponds to the length of a standard deviation of a diffraction limited spot in the image.

In some cases, a computer may be used to control excitation of the switchable entities and the acquisition of images of the swichable entities. In one set of embodiments, a sample may be excited using light having various wavelengths and/or intensities, and the sequence of the wavelengths of light used to excite the sample may be correlated, using a computer, to the images acquired of the sample containing the switchable entities. For instance, the computer may apply light having various wavelengths and/or intensities to a sample to yield different average numbers of activated switchable elements in each region of interest (e.g., one activated entity per location, two activated entities per location, etc). In some cases, this information may be used to construct an image of the switchable entities, in some cases at sub-diffraction limit resolutions, as noted above.

In other aspects of the invention, the systems and methods described herein may also be combined with other imaging techniques known to those of ordinary skill in the art, such as high-resolution fluorescence in situ hybridization (FISH) or immunofluorescence imaging, live cell imaging, confocal imaging, epi-fluorescence imaging, total internal reflection fluorescence imaging, etc.

The following documents are incorporated herein by reference: U.S. patent application Ser. No. 12/012,524, filed Feb. 1, 2008, entitled "Sub-Diffraction Image Resolution and other Imaging Techniques," published as U.S. Pat. Apl. Pub. No. 2008/0182336 on Jul. 31, 2008; International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008; U.S. patent application Ser. No. 11/605,842, filed Nov. 29, 2006, entitled "Sub-Diffraction Image Resolution and other Imaging Techniques," published as U.S. Pat. Apl. Pub. No. 2008/0032414 on Feb. 7, 2008; U.S. Provisional Patent Application Ser. No. 60/836,167, filed Aug. 7, 2006, entitled "Sub-Diffraction Image Resolution"; U.S. Provisional Patent Application Ser. No. 60/836,170, filed Aug. 8, 2006, entitled "Sub-Diffraction Image Resolution"; and U.S. Provisional Patent Application Ser. No. 61/008,661, filed Dec. 21, 2007, entitled "Sub-Diffraction Limit Image Resolution in Three Dimensions."

The following examples are intended to illustrate certain embodiments of the present invention, but do not exemplify the full scope of the invention.

EXAMPLE 1

This example demonstrates 3-dimensional imaging with a spatial resolution that is about 10 times better than the diffraction limit in all three dimensions without invoking sample or optical beam scanning. In International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008, incorporated herein by reference, the photoswitchable nature of certain fluorophores was used to separate the otherwise spatially overlapping images of numerous molecules, and high degrees of localization were achieved in the lateral dimensions for individual fluorescent dyes.

However, this example, and the following examples, illustrates imaging in all three dimensions by stochastic activation of an optically resolvable subset of photo switchable probes, determination of the coordinates for each probe with high accuracy, and construction of a three-dimensional high-resolution image through multiple activation cycles. In some cases, while the lateral position of a particle (or other suitable object) can be determined from the centroid of its image, the shape of the image may also contain information about the particle's axial or z position.

This example uses astigmatism imaging to achieve three-dimensional imaging, although other techniques including but not limited to off-focus imaging, multi-focal plane imaging, and the like, could be used in other cases. To this end, a weak cylindrical lens was introduced into the imaging path to create two slightly different focal planes for the x and y directions (FIG. 1A). This figure shows the three-dimensional localization of individual fluorophores. The simplified optical diagram illustrates the principle of determining the z-coordinate of a fluorescent object from the ellipticity of its image by introducing a cylindrical lens into the imaging path. The right panel shows the images of a fluorophore at various z positions.

As a result, the ellipticity and orientation of a fluorophore's image varied as its position changed in z: when the fluorophore was in the average focal plane (approximately half-way between the x and y focal planes, where the point-spread-function (PSF) has essentially equal widths in the x and y directions), the image appeared round; when the fluorophore was above the average focal plane, its image was more focused in the y direction than in the x direction and thus appeared ellipsoidal with its long axis along x; conversely when the fluorophore was below the focal plane, the image appeared ellipsoidal with its long axis along y. By fitting the image with a two-dimensional elliptical Gaussian function, the x and y coordinates of the peak position could be obtained, as well as the peak widths $w_x$ and $w_y$, which in turn allowed the z coordinate of the fluorophore to be determined.

Figure 1C:
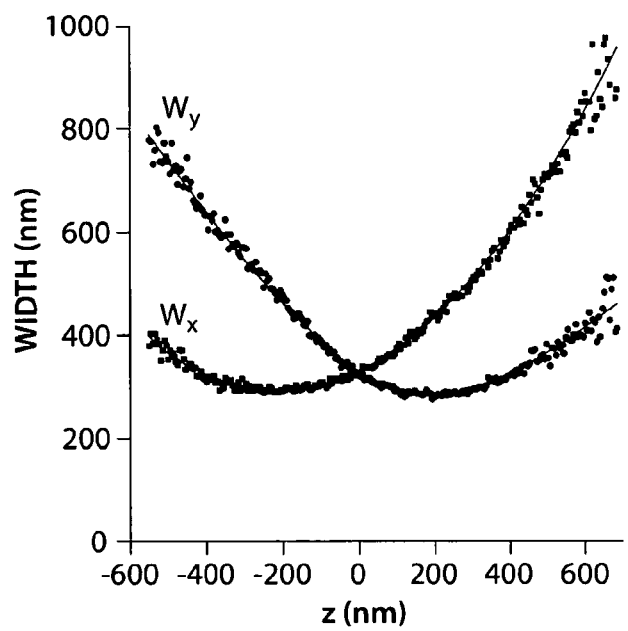

To experimentally generate a calibration curve of $w_x$ and $w_y$ as a function of z, Alexa 647-labeled streptavidin molecules were immobilized on a glass surface and individual molecules were imaged to determine the $w_x$ and $w_y$ values as the sample was scanned in z (FIG. 1C). FIG. 1C is the calibration curve of the image widths $w_x$ and $w_y$ as a function of z obtained from single Alexa 647 molecules in this example. Each data point represents the average value obtained from 6 molecules. The data were fit to a defocusing function (red curve) as described below.

In this image analysis, the z coordinate of each photoactivated fluorophore was determined by comparing the measured $w_x$ and $w_y$ values of its image with the calibration curves. In addition, for samples immersed in aqueous solution on a glass substrate, all z localizations were resealed by a factor of 0.79 to account for the refractive index mismatch between glass and water (see below for additional details).

In some cases, the three-dimensional resolution of the techniques in this example were limited by the accuracy with which individual photoswitchable fluorophores could be localized in all three dimensions during a switching cycle. International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008, incorporated herein by reference, discloses a family of photoswitchable cyanine dyes (Cy5, Cy5.5, Cy7 and Alexa Fluor 647) that can be reversibly cycled between a fluorescent and a dark state by light of different wavelengths. The reactivation efficiency of these photo-switchable "reporters" depends critically on the proximity of an "activator" dye, which can be any one of a variety of dye molecules (e.g. Cy3, Cy2, Alexa Fluor 405). In this particular example, Cy3 and Alexa 647 were used as the activator and reporter pair to perform imaging. A red laser (657 nm) was used to image Alexa 647 molecules and deactivate them to the dark state, whereas a green laser (532 nm) was used to reactivate the fluorophores. Each activator-reporter pair could be cycled on and off hundreds of times before permanent photobleaching occurred, and an average of 6000 photons were detected per switching cycle using objective-type total-internal-reflection fluorescence (TIRF) or epi-fluorescence imaging geometry. This reversible switching behavior provides an internal control to measure the localization accuracy.

Figure 1D:
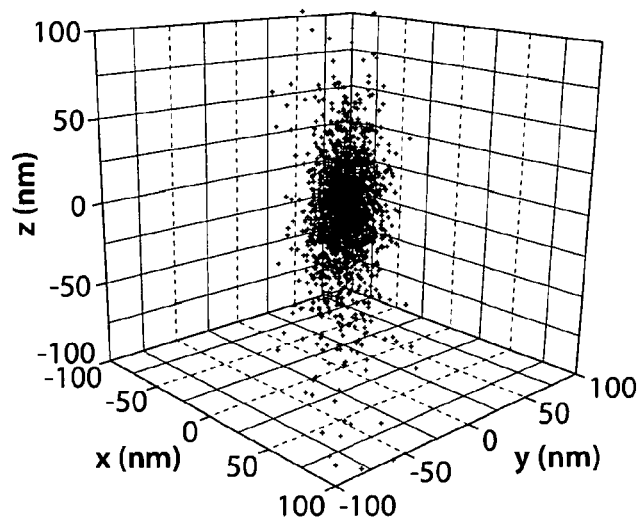
Figure 1E:
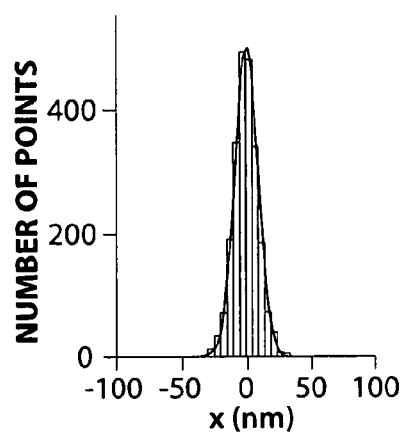
Figure 1F:
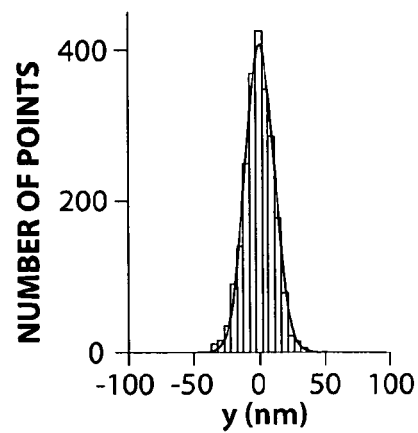
Figure 1G:
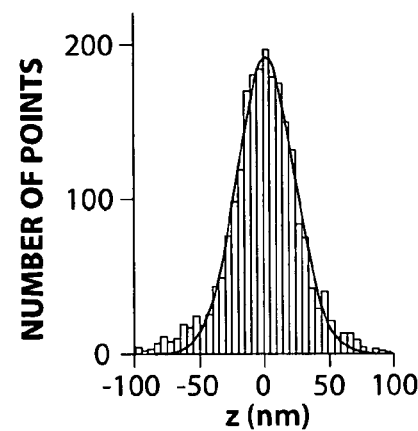

In some experiments, streptavidin molecules doubly labeled with Cy3 and Alexa 647 were immobilized on a glass surface. The molecules were then switched on and off for multiple cycles, and their x, y, and z coordinates were determined for each switching cycle. This procedure resulted in a cluster of localizations for each molecule (FIG. 1D). In this figure, each molecule gives a cluster of localizations due to repetitive activation of the same molecule. Localizations from 145 clusters were aligned to their center-of-mass to generate the overall 3D presentation of the localization distribution (left panel). Histograms of the distribution in x, y and z (right panels) were fit to a Gaussian function, yielding the standard deviation of 9 nm in x, 11 nm in y, and 22 nm in z. The standard deviation (SD: 9 nm in x, 11 nm in y, and 22 nm in z) or full-width-half-maximum (FWHM: 21 nm in x, 26 nm in y, and 52 nm in z) of the localization distribution provided a quantitative measure of localization accuracy in 3 dimensions (FIG. 1E-1G). The localization accuracies in the two lateral dimensions were similar to previous resolutions obtained without the cylindrical lens. The localization accuracy in z was approximately twice those in x and y in these experiments. Because the image width increased as the fluorophore moves away from the focal plane, the localization accuracy decreased with increasing z values, especially in the lateral dimensions. Thus, in some experiments, a, z imaging depth of about 600 nm near the focal plane was chosen, within which the lateral and axial localization accuracies changed by less than 1.6 fold and 1.3 fold, respectively, in comparison with the values obtained at the average focal plane. The imaging depth may, however, be increased, e.g., by employing z scanning in future experiments.

As an initial test, a model bead sample was imaged. The model bead sample was prepared by immobilizing 200 nm biotinylated polystyrene beads on a glass surface and then incubating the sample with Cy3-Alexa 647 labeled streptavidin to coat the beads with photoswitchable probes. Three-dimensional images of the beads were obtained by iterative, stochastic activation of sparse subsets of optically resolvable Alexa 647 molecules, allowing the x, y and z coordinates of individual molecules to be determined. Over the course of multiple activation cycles, the positions of numerous fluorophores were determined and used to construct a full three-dimensional image. The projections of the bead images appeared approximately spherical when viewed along all three directions with average diameters of 210±16, 225±25 and 228±25 nm in x, y and z respectively (FIG. 4), indicating accurate localization in all three dimensions. As the image of each fluorophore simultaneously encodes its x, y and z coordinates, no additional time was required to localize each molecule in three-dimensions as compared with three-dimensional imaging.

FIG. 4 shows three-dimensional images of 200 nm diameter beads coated with Cy3-Alexa 647 labeled streptavidin. FIG. 4A shows the x-z projection of two beads within an area of 1.7 micrometers (x)×10 micrometers (y) on the glass surface. The surface is defined by a line of localizations underneath the beads, resulting from streptavidin molecules non-specifically adsorbed to the glass surface. Although the non-specifically adsorbed streptavidins were only sparsely distributed on the surface, a large area projection results in an almost continuous line of localizations. The inset in FIG. 4A shows the x-z projection of a small volume (400 nm×400 nm×400 nm) surrounding the right bead, where a few non-specifically adsorbed streptavidin molecules were present. FIGS. 4B and 4C show the x-y projection of the two beads. The slight deviation from a round shape may be in part due to the imperfect streptavidin coating and/or the intrinsically non-ideal bead shape.

Figure 4A:
FIGS. 4A-4D illustrate three-dimensional imaging of various beads, in accordance with one embodiment of the invention.
Figure 4B:
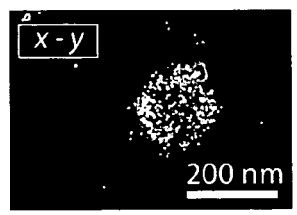
Figure 4C:
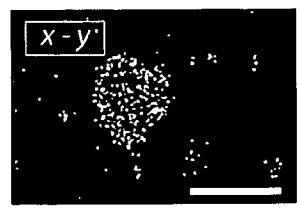
Figure 4D:
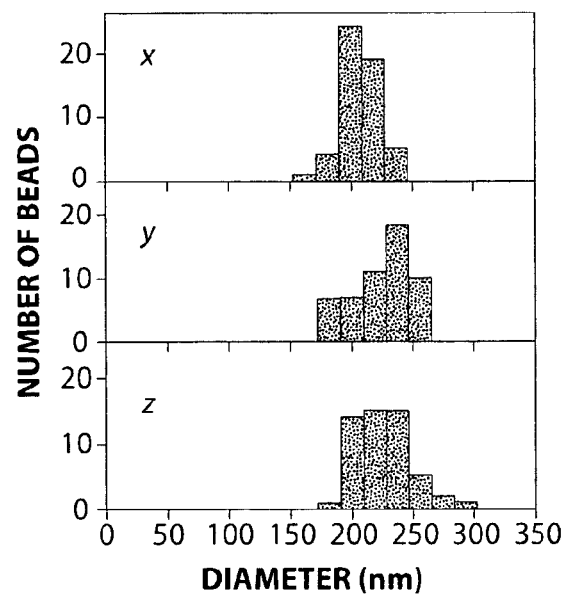

FIG. 4D illustrates the distribution of the bead diameters in the x, y and z directions. To determine the diameters in a non-subjective manner, the streptavidin molecules were assumed to be coated uniformly on the bead surface. Such a 3D uniform distribution on a spherical surface, when projected onto any of the x, y and z axes, should follow a 1D uniform distribution. The width of the 1D distribution in the x, y or z directions provides a measure of the diameter of the bead along the x, y or z axis, respectively. In addition, the mathematical relation between the width (d) and the standard deviation ($SD_{uniform}$) of a uniform distribution can be used in some cases, i.e. $SD_{uniform}^2 = d^2/12$ and the relation between the measured standard deviation $SD_{measure}$ and the $SD_{uniform}$ of the true uniform distribution considering finite localization accuracy ($SD_{localization}$), i.e. $SD_{measure}^2 = SD_{uniform}^2 + SD_{localization}^2$. From the independently measured localization accuracies as shown in FIG. 1E-1F, and the $SD_{measure}$ of the projected distribution of the 3D bead image in the x, y and z directions, the diameters (d) of the beads were deduced along the x, y and z axes. The diameter distributions of 53 measured beads are shown here and the average diameters are 210±16 nm, 226±25 nm, and 228±25 nm in the x, y and z directions, respectively. The measured diameters are quantitatively similar to the manufacturer's suggested diameter (200 nm) for the beads. The slight increase may be in part due to the finite thickness of the streptavidin coating.

Figure 2A:
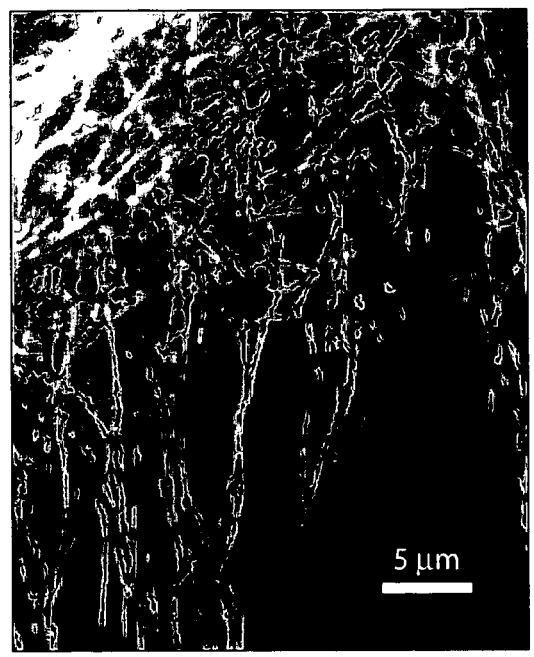
FIGS. 2A-2F illustrates another embodiment of the invention, useful for imaging cells.
Figure 2B:
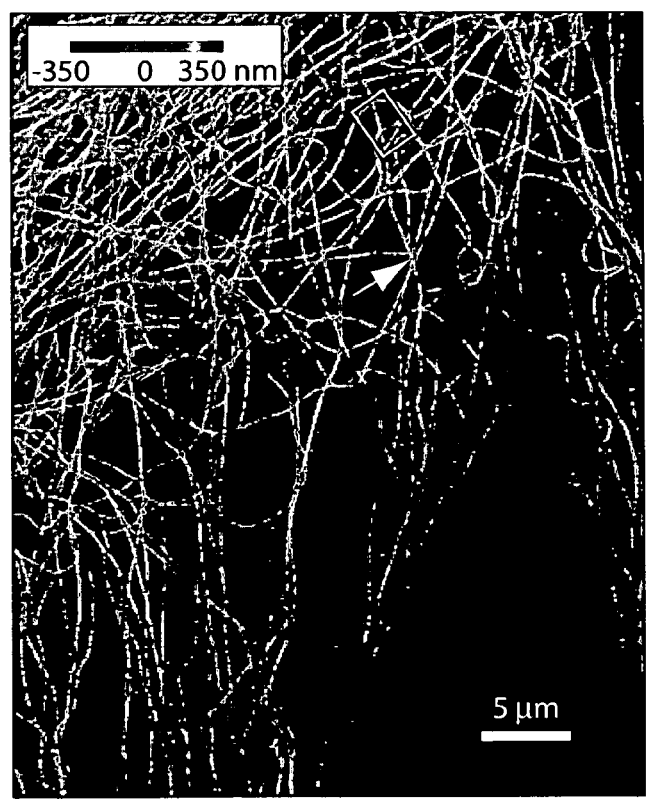
Figure 2C:
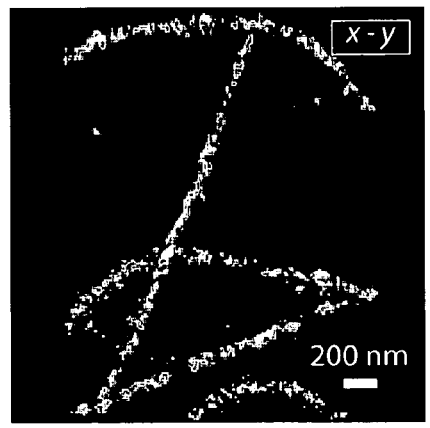
Figure 2D:
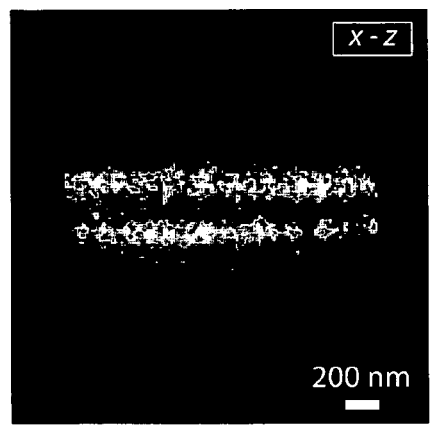
Figure 2E:
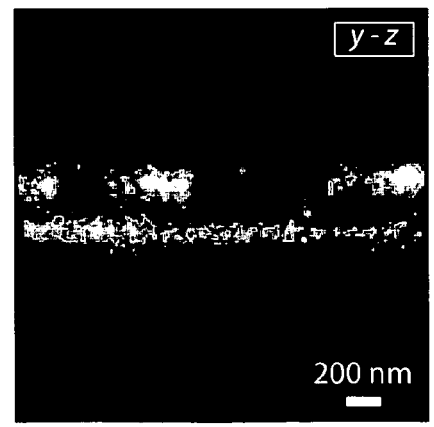

Cell imaging is described as another example. In this example, indirect immunofluorescence imaging was performed of the microtubule network in green monkey kidney epithelial (BS-C-1) cells. Cells were immunostained with primary antibodies and then with Cy3 and Alexa 647 doubly-labeled secondary antibodies. The three-dimensional images that were obtained not only showed a substantial improvement in the resolution as compared to the conventional wide-field fluorescence image (FIGS. 2A-2B), but also provided z-dimension information (FIG. 2B) that was not available in the conventional image (FIG. 2A). FIG. 2A is a conventional indirect immunofluorescence image of microtubules in a large area of a BS-C-1 cell; FIG. 2B is of the same area, imaging using the techniques described herein and shaded according to z-position information. Multiple layers of microtubule filaments were clearly visible in the x-y, x-z or y-z cross sections of the cell (FIGS. 2C-2E). This region is the region outlined by the white box in FIG. 2B, showing 5 microtubule filaments.

Figure 2F:
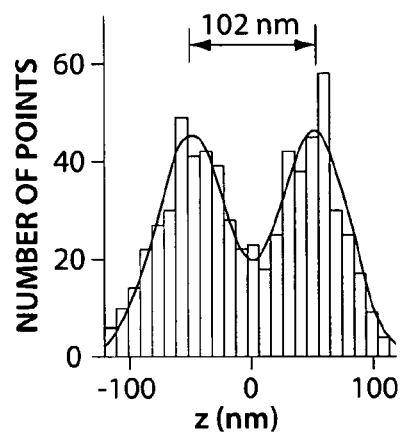

To characterize the cell imaging resolution more quantitatively, point-like objects were identified in the cell that appeared as small clusters of localizations away from any discernable microtubule filaments. These clusters may represent individual antibodies nonspecifically attached to the cell. The FWHM of these clusters, which were randomly chosen over the entire measured z-range of the cell, were 22 nm in x, 28 nm in y and 55 nm in z (FIG. 5), quantitatively similar to those determined for individual molecules immobilized on a glass surface (compare FIG. 5 with FIG. 1E-1G). Two microtubule filaments separated by 102 nm in z appeared well separated in the three-dimensional image (FIG. 2F), which shows the z profile of two microtubules crossing in the x-y projection. This histogram shows the distribution of z-coordinates of the localizations, fit to a double Gaussian with identical width (curve). The apparent width of the microtubule filaments in the z dimension was 66 nm, slightly larger than the intrinsic imaging resolution in z, and quantitatively agreeing with the convolution of the imaging resolution and the independently measured width of antibody-coated microtubule (FIG. 2F). As the effective resolution was determined by a combination of the intrinsic imaging resolution and the size of the labels (such as the antibodies), improvement in the resolution may be achieved by using direct instead of indirect immunofluorescence to remove one layer of antibody labeling, as shown in the next example, or by using Fab fragments or genetically encoded peptide tags to replace antibodies.

Figure 5A:
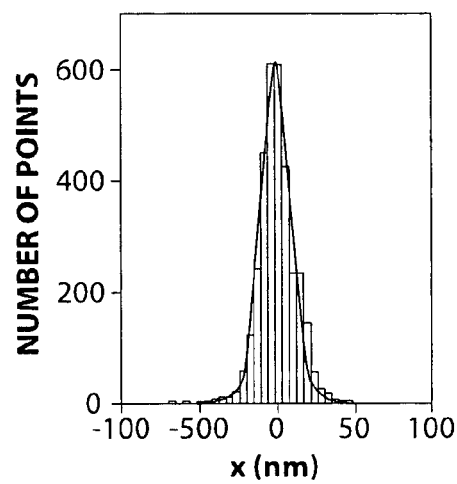
FIGS. 5A-5C illustrate the accuracy of imaging a cell, according to one embodiment of the invention.
Figure 5B:
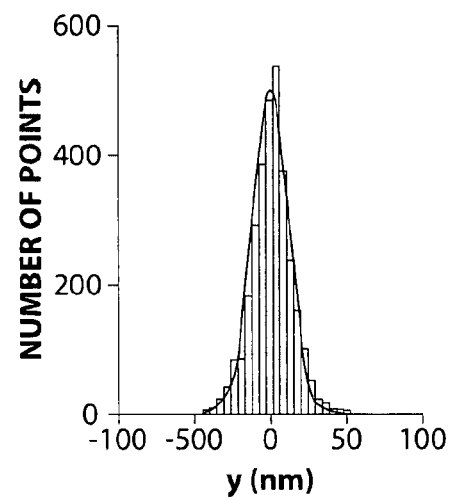
Figure 5C:
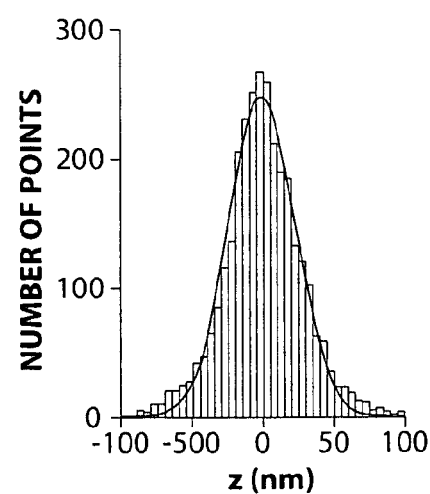
Figure 6A:
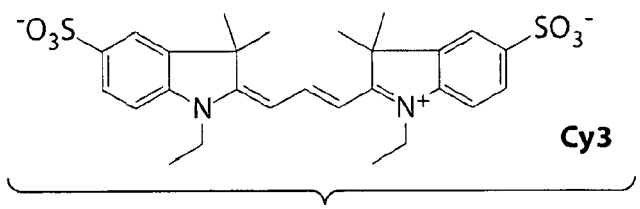
FIGS. 6A-6E illustrate various fluorescent compounds useful in certain embodiments of the invention.
Figure 6B:
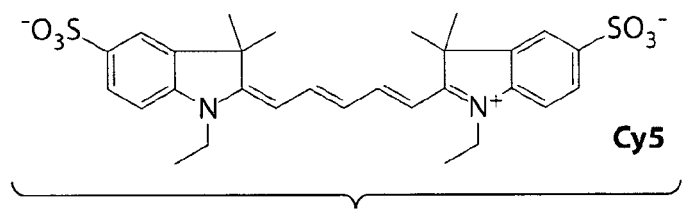
Figure 6C:
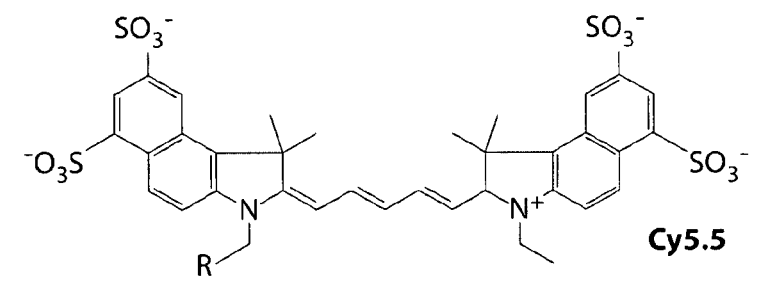
Figure 6D:
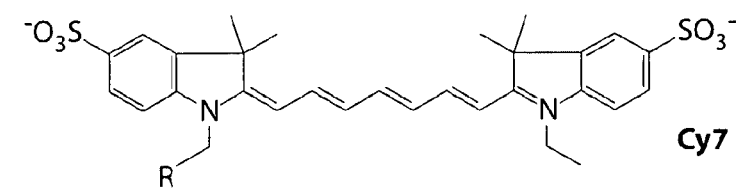
Figure 6E:
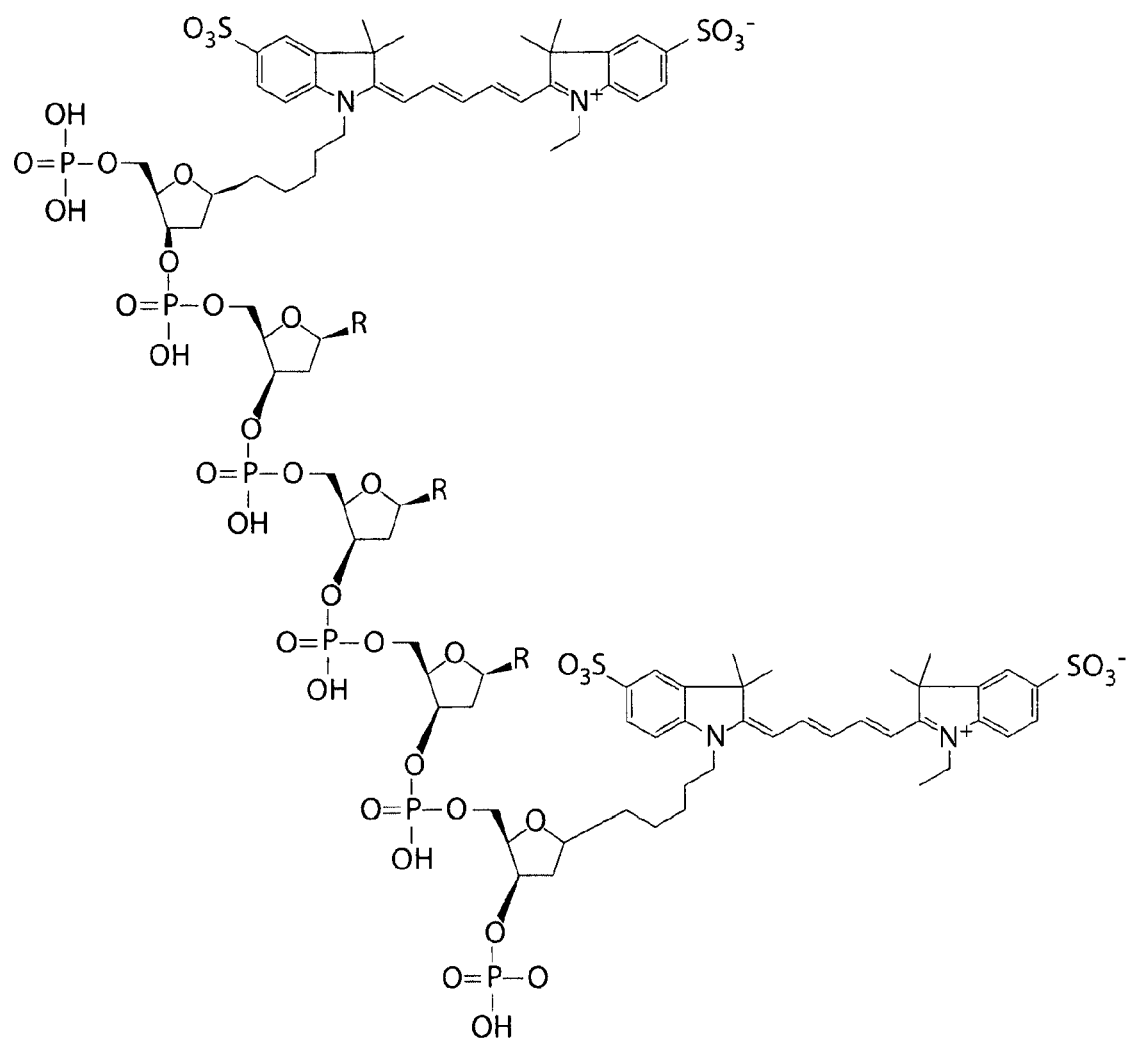

In FIG. 5, the localization accuracy was determined from point-like objects in a cell, which appeared as small clusters of localizations away from any discernable microtubule filaments. Shown here are the spatial distribution of localizations within these point-like clusters in the x, y and z dimensions. The histogram of localizations was generated by aligning 202 clusters by their centers of mass, with each cluster containing ≥8 localizations. Fitting the histograms with Gaussian functions gives standard deviations of 9 nm, 12 nm, and 23 nm in the x, y and z directions, respectively. The corresponding FWHM values were 22 nm, 28 nm and 55 nm.

Figure 3A:
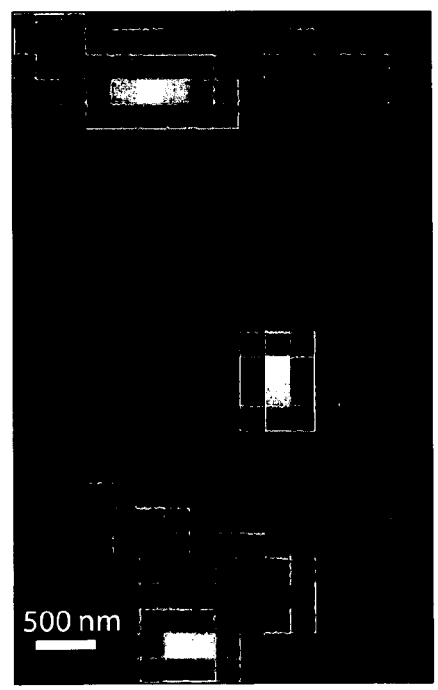
FIGS. 3A-3H illustrate three-dimensional imaging of a cell, according to another embodiment of the invention.
Figure 3B:
Figure 3C:
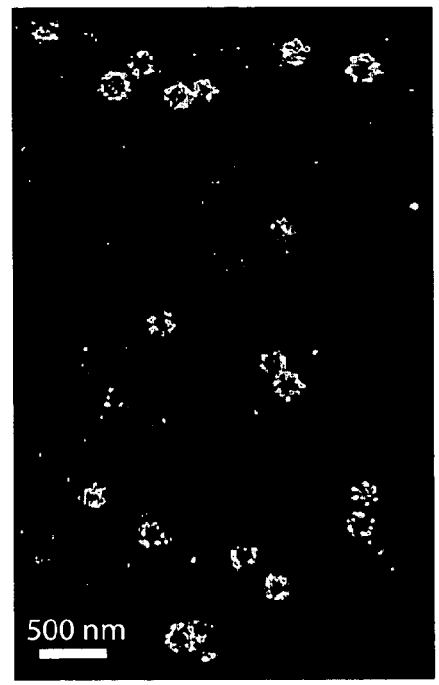
Figure 3D:
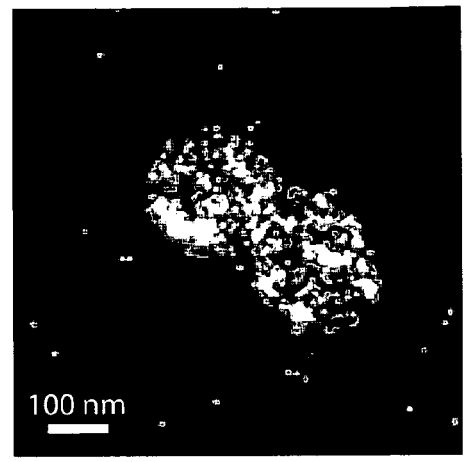
Figure 3E:
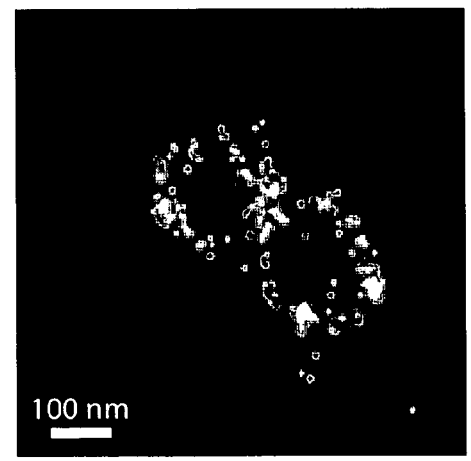
Figure 3F:
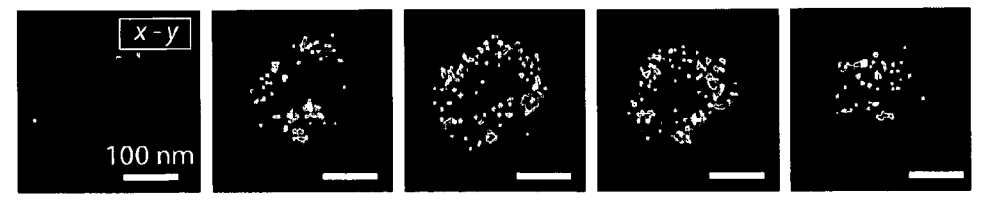
Figure 3G:
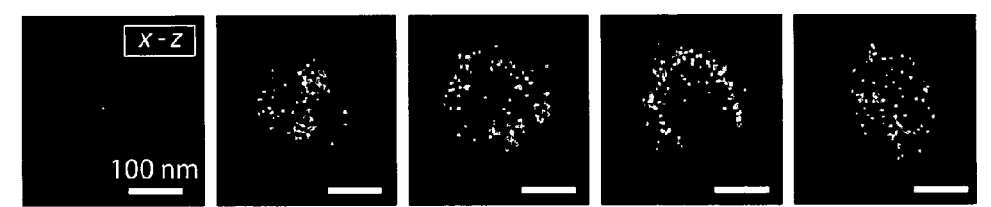
Figure 3H:
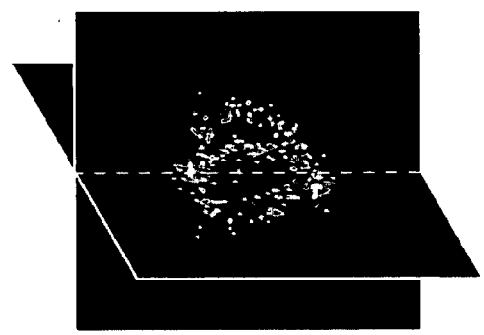

Finally, to demonstrate that the three-dimensional morphology of nanoscopic structures in cells could be resolved, clathrin-coated pits (CCP) were imaged in BS-C-1 cells. CCPs are 150 nm to 200 nm spherical cage-like structures assembled from clathrin, adaptor proteins and other cofactors on the cytoplasmic side of the cell membrane to facilitate endocytosis. To image CCPs, a direct immunofluorescence scheme was used, using the Cy3 and Alexa 647 doubly-labeled primary antibodies for clathrin. When imaged by conventional fluorescence microscopy, all CCPs appeared as nearly diffraction-limited spots with no discernable structure (FIG. 3A, which is a conventional direct immunofluorescence image of a region of a BS-C-1 cell). In two-dimensional images using the techniques described herein in which the z-dimension information was discarded, the round shape of CCPs was observable (FIGS. 3B and 3D). The size distribution of CCPs measured from the 2D projection image, 180±40 nm, agrees quantitatively with the size distribution determined using electron microscopy. Including the z-dimension information allows the visualization of the 3D structure of the pits (FIGS. 3C and 3E-3H). FIGS. 3C and 3E show the x-y cross-sections of the image, taken from a region near the opening of the pits at the cell surface. FIG. 3C is a 50 nm thick x-y cross-section of the same area as shown in FIGS. 3A-3B, showing the ring-like structure of the opening of the CCPs at the plasma membrane, while FIG. 3E is a magnified view of the 100 nm thick x-y cross-section of two nearby CCPs.

The circular ring-like structure of the pit periphery was unambiguously resolved. The consecutive x-y and x-z cross-sections of the pits (FIGS. 3F-3H) revealed the three-dimensional half-spherical-cage like morphology of these nanoscopic structures that was not observable in the two-dimensional images. These figures show x-y cross-sections (each 50 nm thick in z) (FIG. 3F) and the serial x-z cross-sections (each 50 nm thick in y) (FIG. 3G) of a CCP, and an x-y and x-z cross section presented in 3D perspective (FIG. 3H), showing the half-spherical-cage like structure of the pit.

In summary, these examples illustrate three-dimensional, high-resolution imaging with resolutions on the order of 100 nm or less. Nanoscale features of cellular structures were resolved at a resolution previously only seen with electron microscopy, and now optically with molecular specificity under ambient conditions. This development may significantly enhance the ability to visualize molecular organization and interaction networks in cells.

EXAMPLE 2

This example describes certain techniques useful with respect to Example 1. To characterize the 3D localization accuracy of the photoswitchable probes of Example 1, streptavidin molecules (Invitrogen) were labeled with photoswitchable Alexa 647 fluorophore (Invitrogen) and the activator dye Cy3 (GE Healthcare) by incubating the protein with amine-reactive dyes following the suggested protocol from the manufacturers. Unreacted dye molecules were removed by gel filtration using a Nap-5 column (GE Healthcare). The labeling ratio was characterized by a UV-Vis spectrophotometer, and the absorption spectrum indicated a labeling ratio of ~2 Cy3 and ~0.1 Alexa 647 per streptavidin molecule. The labeled streptavidin was then immobilized onto the surface of a glass flow chamber assembled from a glass slide and a #1.5 coverglass. Slides and coverglasses were cleaned by sonicating in 1 M potassium hydroxide for 15 min, followed by extensive washing with MilliQ water and drying with compressed nitrogen. The labeled streptavidin sample was injected into the flow chamber to allow the streptavidin to adsorb directly on the surface non-specifically or through a biotin-streptavidin linkage on the biotinylated bovine serum albumin (BSA) coated surface. To generate the calibration curve for z localization measurement, Alexa 647-labeled streptavidin or quantum dots (Protein A coated Qdot 655, Invitrogen) were also used. The singly labeled streptavidin were immobilized to the chamber surfaces in a similar manner as the Cy3 and Alexa 647 doubly-labeled streptavidin and the quantum dots were immobilized directly to the surface by nonspecific binding.

To make 200 nm polystyrene beads coated with photoswitchable fluorophores, the coverglass surface was first coated with streptavidin by flowing 0.25 mg/mL unlabeled streptavidin solution into the flow chamber as described above and then rinsed with phosphate buffered saline (PBS). Next, 200 nm diameter biotinylated polystyrene beads (Invitrogen) were added to the chamber to allow immobilization on the surface. Finally 3 micrograms/mL Cy3 and Alexa 647 doubly streptavidin labeled were flowed in to coat the surface of the biotinylated beads. During this procedure, some fluorescent streptavidin also adsorbed non-specifically onto the coverglass surface. The flow chamber was then rinsed with PBS to remove free streptavidin molecules in solution.

BS-C-1 cells were plated in 8-well chambered coverglasses (LabTek-II, Nalgene Nunc) at a density of 40 k cells per well. After 16 to 24 hours, the cells were fixed using 3% paraformaldehyde and 0.1% glutaraldehyde in PBS for 10 min, and then treated with 0.1% sodium borohydride for 7 min to reduce the unreacted aldehyde groups and fluorescent products formed during fixation. The sodium borohydride solution was prepared immediately before use to avoid hydrolysis. The fixed sample was then washed three times with PBS, and permeabilized in blocking buffer (3% w/v BSA, 0.5% v/v Triton X-100 in PBS) for 15 min.

Microtubules were stained with mouse monoclonal β-tubulin antibodies (ATN01, Cytoskeleton) for 30 min and then goat anti-mouse secondary antibodies for 30 min. The secondary antibodies were labeled with amine-reactive Alexa 647 and Cy3 and the labeling stoichiometry was characterized to be ~4.0 Cy3 and ~0.4 Alexa 647 per antibody on average. Three washing steps using 0.2% w/v BSA and 0.1% v/v Triton-X100 in PBS were performed after each staining step.

For staining clathrin by direct immunofluorescence, mouse monoclonal anti-clathrin heavy chain (clone X22, ab2731, Abcam) and anti-clathrin light chain (clone CON.1, C1985, Sigma-Aldrich) were used simultaneously. Both antibodies were labeled with ~1.0 Cy3 and ~1.0 Alexa 647 per antibody. The sample was stained for 30 min, washed three times with PBS and used immediately for imaging.

It should be noted that the immunofluorescence imaging can work well at a wide range of dye-labeling ratios. Typically a labeling ratio of ≥1 activator (Cy3 in this case) per antibody was chosen to ensure that the majority of antibodies had activators. On the other hand, when more than one photoswitchable reporter (Alexa 647 in this case) were attached to amino acid residues within close proximity on the same antibody, the reporter-reporter interaction can result in a significantly lower rate of switching off in some cases. Previous characterizations have indicated that the off rate of two reporters separated by 2 nm was ~5 times slower than that of a single reporter whereas the two reporters separated by 7 nm have comparable off rate as that of an isolated reporter. Therefore, a dye/protein ratio of ≤1 was chosen for the reporter to minimize this effect.

Buffer solutions in the samples were replaced with an imaging buffer immediately before data acquisition. The imaging buffer contained 50 mM Tris, pH 7.5, 10 mM NaCl, 0.5 mg/mL glucose oxidase (G2133, Sigma-Aldrich), 40 micrograms/mL catalase (106810, Roche Applied Science), 10% (w/v) glucose and 1% (v/v) beta-mercaptoethanol. It was found that beta-mercaptoethanol (or other thiol-containing reagents such as cysteine) were important for photoswitching of the cyanine dyes. Imaging may also be performed at lower beta-mercaptoethanol concentrations (e.g. 0.1% v/v), which are compatible with live cell imaging. In this work, all of the imaging experiments described above were performed on fixed cells.

All of the imaging experiments described in Example 1 were performed on an inverted optical microscope (Olympus IX-71). Two solid state lasers were used as the excitation source: a 657 nm laser (RCL-200-656, Crystalaser) for exciting the photo-switchable reporter fluorophore (Alexa 647) and switching it to the dark state; and a 532 nm laser (GCL-200-L, Crystalaser) for reactivating the Alexa 647 in a Cy3-facilitated manner. The two laser beams were combined and coupled into an optical fiber (P3-630A-FC-5, Thorlabs). The fiber output was collimated and focused onto the back focal plane of a high numerical aperture oil immersion objective (100x UPlanSApo, NA 1.4, Olympus) through the back port of the microscope. A translation stage allowed both lasers to be shifted towards the edge of the objective so that the emerging light from the objective reached the sample at a high incident angle near but not exceeding the critical angle of the glass-water interface. This excitation scheme allowed fluorophores within a few micrometers from the surface to be excited and reduced the background fluorescence from the solution. The fluorescence emission was collected by the same objective and filtered by a polychroic mirror (z458/514/647rpc, Chroma), a band pass filter (HQ710/70m, Chroma) and a long pass filter (HQ665LP, Chroma). The filtered emission was then imaged onto an EMCCD camera (Ixon DV897DCS-BV, Andor) through a pair of relay lenses with a weak cylindrical lens (1 m focal length) inserted in between.

To stabilize the microscope focus during data acquisition, the reflected red excitation laser from the glass-water interface was directed onto a quadrant photodiode by a reflective prism at the back port of the microscope. The quadrant photodiode read the position of the reflected laser, which is sensitive to the distance between the coverglass surface and the objective. This information was then fed back to a z-positioning piezo stage (NanoView-M, MadCity Labs) by software to correct for the z-drift in the microscope focus. This "focus lock" system was capable of maintaining the focus position within 40 nm for the duration of STORM data acquisition. Residual drift in z was corrected during data analysis, as described below.

During data acquisition, a relatively strong imaging/deactivation laser (~40 mW at 657 nm) and a relatively weak activation laser (<2 microwatts at 532 mm) were applied to the sample simultaneously. The simultaneous illumination with both the activation and deactivation lasers resulted in the stochastic switching of the reporter fluorophores between the fluorescent and dark states. A relatively strong imaging/deactivation laser power was chosen to ensure high emission intensity and a rapid switching off rate, and the relatively weak activation laser was chosen to ensure that the fraction of activated fluorophores at any given time was sufficiently low so that they were optically resolvable. The EMCCD camera acquired the images continuously at a frame rate of 20 Hz to obtain a "movie."

In order to derive the z coordinates from the widths of the single molecule images, calibration curves were generated as shown in FIG. 1C. The calibration experiments were performed in Example 1 in three ways: 1. Alexa 647 labeled streptavidin was adsorbed on the coverglass surface at a low density such that individual streptavidin molecules were resolvable from each other. The beta-mercaptoethanol in the imaging buffer was replaced with 2 mM Trolox so that blinking of the fluorophore was suppressed. The fluorescence images of individual streptavidin molecules were recorded while scanning the sample stage in z at a constant rate with the piezo stage. 2. Quantum dots were adsorbed onto the coverglass. A solution of 1% beta-mercaptoethanol in PBS was used as the imaging buffer to suppress the blinking of quantum dots. The fluorescence images of individual quantum dots were acquired while scanning the sample stage in z at a constant rate. 3. Cy3-Alexa 647 labeled streptavidin was adsorbed on the coverglass surface with high density. The measurement was performed in the same way as during data acquisition except that the sample was scanned slowly in z at a constant rate. Photoactivation events in a small area (usually 8 micrometers×4 micrometers) within the view field were used for measuring the calibration curve. All three measurements produced similar calibration curves.

Fluorescent peaks in one image frame of a calibration experiment were fit with an elliptical Gaussian function $$G(x, y) = h \exp\left(-2\frac{(x-x_0)^2}{w_x^2} - 2\frac{(y-y_0)^2}{w_y^2}\right) + b$$

where h is the peak height, b is the background, $(x_0, y_0)$ is the center position of the peak, and $w_x$ and $w_y$ stand for the widths of the image (point spread function, PSF) in the x and y directions, respectively. At the same time, the z position of the corresponding molecule was determined from the z trajectory of the piezo stage. The $w_x$ and $w_y$ values as a function of z were then fit to a modified form of a typical defocusing curve:

$$w_{x,y}(z) = w_0 \sqrt{1 + \left(\frac{z-c}{d}\right)^2 + A\left(\frac{z-c}{d}\right)^3 + B\left(\frac{z-c}{d}\right)^4}$$

where $w_0$ is the PSF width when a molecule is at the focal plane, c is the offset of the x or y focal plane from the average focal plane, d is the focus depth of the microscope, and A and B are coefficients of higher order terms to correct for the non-ideality of the imaging optics. The average focal plane is defined such that a fluorophore positioned in this plane has an image PSF with equal widths in the x and y directions, thus generating a spherical image. It should be noted that these fitting curves were generated to facilitate the automated z-localization when the measured $w_x$ and $w_y$ values were compared with the calibration curve to search for the corresponding z position. The exact function used for the fitting curve was unimportant as long as the curves fit the measured calibration data with sufficient precision.

The data were analyzed in a similar manner as described previously (see International Patent Application No. PCT/US2007/017618, filed Aug. 7, 2007, entitled "Sub-Diffraction Limit Image Resolution and Other Imaging Techniques," published as Int. Pat. Apl. Pub. No. WO 2008/091296 on Jul. 31, 2008, incorporated herein by reference) but now with the additional z-dimension information derived from the shape of the image of individual activated fluorophores. Fluorescent peaks in each image frame of the STORM movie were identified by fitting local maxima with an elliptical Gaussian function to deduce the peak height h', the center position in the two lateral dimensions, $x_0'$ and $y_0'$, and the peak widths in the two lateral dimensions, $w_x'$ and $w_y'$. Applying a threshold to the peak height (h'), width ($\sqrt{w_x' w_y'}$) and ellipticity ($w_x'/w_y'$), peaks that were rejected were too weak, too wide or too skewed to yield satisfactory localization accuracy. Also rejected were certain peaks that would have resulted in overlapping images of multiple fluorophores. If the center positions of identified peaks in consecutive frames were spatially separated by less than one pixel, they were considered as originating from the same molecule during one photoactivation event. All images from the same photoactivation event of the same fluorophore in different frames were averaged and a second fit to an elliptical Gaussian function was performed to deduce the refined center positions $x_0$ and $y_0$, and widths $w_x$ and $w_y$. The area of the image used for the second fit was determined by the peak widths obtained in the initial fit.

After the second fit, the calibration curve was searched to find a $z_0$ point that best matched the measured widths $w_x$ and $w_y$ obtained from the fit. This search was performed automatically by minimizing the distance in the $w_x^{1/2}$–$w_y^{1/2}$ space:

$$D = \sqrt{(w_x^{1/2} - w_{x,calib}^{1/2})^2 + (w_y^{1/2} - w_{y,calib}^{1/2})^2}$$

It can be shown by simulation and by an analytical treatment that using the square root of the widths improves the accuracy of localization in z in the search procedure as compared to using the widths directly. Activation events with a minimum distance D larger than a preset threshold indicated that the image was distorted, most likely caused by more than one molecule located in close proximity and photoactivated in the same image frame. These events were rejected from further analysis. This procedure allowed the 3D position ($x_0$, $y_0$ and $z_0$) of each activated fluorophore to be obtained and in this manner the three-dimensional image was constructed.

When performing 3D STORM measurements of biological samples in aqueous solutions supported by glass substrates using an oil immersion objective, the mismatch of indices of refraction between glass (n=1.515) and the imaging buffer (n=1.35 for 10% glucose solution) may be considered. This index of refraction mismatch effectively shifts the apparent z position of an object away from the glass surface. Within a few micrometers from the surface, it was shown that this refractive-index-mismatch induced magnification of the z-distance can be treated as a constant and that the magnification factor is equal to 1.26 for the objective and refractive indexes used in these imaging condition (objective: NA=1.4, glass: n=1.515 and buffer: n=1.35). This small magnification effect was corrected accordingly in the z-localization analysis by rescaling all z values, obtained from direct comparison with the calibration curve, by a factor of 1/1.26=0.79.

Due to aberrations in the imaging optics, the PSF may become asymmetric when a fluorophore is out of focus, and as a result, the center of its image may deviate slightly from the actual lateral position of the fluorophore. This causes an apparent tilting distortion in the 3D image. The average tilt was typically not more than 4 degrees in these experiments and can be corrected by pre-calibration of the tilt profile.

An important factor that affects the localization accuracy is the sample stage drift during the image acquisition time, including both drift in x-y plane and drift in the z direction. In the setup used in Example 1, a focus lock was installed to minimize z-drift, but a residue drift of ~40 nm is present. The drift was corrected using two methods in these examples. One method involves adding fiducial markers (fluorescent beads) to track the drift of the sample and subtracting the movement of the markers during image analysis. The other method used the correlation function of the image for drift correction. The second method was used to correct for the x, y and z drift in the above examples. A movie was divided in time into equal-period segments and an image was constructed from each movie segment. The correlation functions between the image in the first segment and all subsequent segments were then calculated and the centroid positions of the correlation functions were determined. Interpolations based on these centroid positions were used to generate a curve of the centroid position as a function of time for each imaging frame. This drift was then subtracted from the localizations and all localizations at different time points were included to generate the drift corrected image.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   providing a plurality of entities able to emit light, at least some of which are separated by a distance of less than about 1000 nm;
   activating a fraction of the plurality of entities to emit light;
   forming an astigmatism image of the fraction of the plurality of entities by an optical system which produces astigmatic aberration with respect to the direction that the emitted light passes through the lens;
   determining the astigmatism image;
   deactivating the activated fraction of the plurality of entities; and
   repeating the acts of activating, forming, determining, and deactivating to determine x, y, and z positions of the plurality of entities based on the plurality of astigmatism images, wherein the x, y, and z positions of the plurality of entities are 3-D spatial coordinates and are each determined to a precision better than the wavelength of the light emitted by some of the plurality of entities.

2. A method, comprising:
   providing a plurality of entities able to emit light;
   activating a fraction of the plurality of entities to emit light;
   forming an astigmatism image of the fraction of the plurality of entities by an optical system which produces astigmatic aberration with respect to the direction that the emitted light passes through the lens;
   determining the astigmatism image;
   deactivating the activated fraction of the plurality of entities; and
   repeating the acts of activating, forming, determining, and deactivating to determine x, y, and z positions of the plurality of entities based on the plurality of astigmatism images, wherein the x, y, and z positions of the plurality of entities are 3-D spatial coordinates and are each determined to a precision better than the wavelength of the light emitted by some of the plurality of entities.

3. The method of claim 2, wherein at least some of the plurality of entities are separated by a distance of separation less than the wavelength of the emitted light.

4. The method of claim 2, further comprising constructing an image of the plurality of entities using their respective x, y, and z positions.

5. The method of claim 2, further comprising determining the z positions of the plurality of entities from the shapes of their images at a detector.

6. The method of claim 2, further comprising determining the z positions of the plurality of entities from the intensities of their images at a detector.

7. The method of claim 2, wherein the optical system includes a lens that is non-circularly symmetric with respect to the direction of light emitted by the some of the plurality of entities passes through the lens.

8. The method of claim 7, wherein the lens that is non-circularly symmetric is a cylindrical lens.

9. The method of claim 2, wherein the astigmatism image is formed at a detector, and some of the fraction of the plurality of entities is not focused at the detector.

10. The method of claim 2, wherein the plurality of astigmatism images are formed at a plurality of detectors, and some of the fraction of the plurality of entities are not in a focal region of at least one of the plurality of detectors.

11. The method of claim 2, wherein the optical system defines a focal region that does not contain at least a portion of the fraction of the plurality of entities.

12. The method of claim 2, wherein the astigmatism image is formed at a detector, and at least a portion of the fraction of the plurality of entities is not in a conjugate plane of the detector.

13. The method of claim 2, wherein the plurality of astigmatism images are formed at a plurality of detectors, and at one or more of the plurality of detectors, at least a portion of the fraction of the plurality of entities is not focused.

14. The method of claim 2, wherein at least some of the plurality of entities emit light at different wavelengths.

15. The method of claim 2, wherein the plurality of entities each emit light at substantially the same wavelength.

16. The method of claim 2, wherein at least some of the plurality of entities are activated by light at different wavelengths.

17. The method of claim 2, wherein the plurality of entities are each activated by light at substantially the same wavelength.

18. The method of claim 2, wherein at least some of the plurality of entities are photoactivatable or photoswitchable probes.

19. The method of claim 2, wherein the light emitted by at least some of the plurality of entities has a wavelength of between about 400 nm and about 1000 nm.

20. The method of claim 2, wherein the x, y, and z positions of the plurality of entities are each determined to a precision better than about 300 nm.

21. The method of claim 2, wherein the x, y, and z positions of the plurality of entities are each determined to a precision better than about 100 nm.

22. The method of claim 2, wherein the x, y, and z positions of the plurality of entities are each determined to a precision better than about 50 nm.

23. The method of claim 2, wherein the x, y, and z positions of the plurality of entities are each determined to a precision better than about 20 nm.

24. The method of claim 2, wherein the x, y, and z positions of the plurality of entities are each determined to a precision better than about 10 nm.

25. The method of claim 2, comprising determining the positions of the plurality of entities at a first point of time, and determining the positions of the plurality of entities at a second point of time.

26. The method of claim 2, comprising determining the positions of the plurality of entities at more than one point of time or as a function of time or both.

27. The method of claim 2, wherein the acts are performed in the order recited.

* * * * *